United States Patent [19]

Ginsberg et al.

[11] Patent Number: 5,523,209

[45] Date of Patent: Jun. 4, 1996

[54] METHODS FOR IDENTIFYING INHIBITORS OF INTEGRIN ACTIVATION

[75] Inventors: Mark H. Ginsberg; Timothy E. O'Toole, both of San Diego, Calif.

[73] Assignee: The Scripps Research Institute, LaJolla, Calif.

[21] Appl. No.: 214,770

[22] Filed: Mar. 14, 1994

[51] Int. Cl.$^6$ .................................................. G01N 33/53
[52] U.S. Cl. ............................ 435/7.2; 435/7.1; 435/7.8; 436/501
[58] Field of Search .......................... 435/7.1, 7.2, 69.7; 436/501

[56] References Cited

U.S. PATENT DOCUMENTS

| | | | |
|---|---|---|---|
| 4,981,784 | 1/1991 | Evans et al. | 435/6 |
| 5,030,576 | 7/1991 | Dull et al. | 435/69.7 |

FOREIGN PATENT DOCUMENTS 9208739  5/1992  WIPO.

OTHER PUBLICATIONS

Adams, et al., Changes in Keratinocyte Adhesion During Terminal Differentiation: Reduction in Fibronectin Binding Precedes $\alpha_5\beta_1$ Integrin Loss from the Cell Surface, Cell 63:425–435 (1990).
Albelda, et al., Integrins and other cell adhesion molecules, FASEB, J. 4:2868–2880 (1990).
Altieri, Occupancy of CD11b/CD18 (Mac-1) Divalent Ion Binding Site(s) Induces Leukocyte Adhesion, The Journal of Immunology 147:1891–1898 (1991).
Altieri, et al., Oligospecificity of the Cellular Adhesion Receptor MAC-1 Encompasses an Inducible Recognition Specificity for Fibrinogen, The Journal of Cell Biology 107:1893–1900 (1988).
Bennett, et al., Exposure of Platelet Fibrinogen Receptors by ADP and Epinephrine, J. Clin. Invest. 64:1393–1401 (1979).
Bennett, et al., Interaction of Fibrinogen with Its Platelet Receptor, The Journal of Biological Chemistry 263:12948–12953 (1988).
Bosco, et al., Multiple Functional Forms of the Integrin VLA-2 Can be Derived from a Single $\alpha^2$ cDNA Clone: Interconversion of Forms . . . The Journal of Cell Biology 120:537–543 (1993).
Burger, et al., Induced Cell Surface Expression of Functional $\alpha_2\beta_1$ Integrin during Megakaryocytic Differentiation of K562 Leukemic Cells, Experimental Cell Research 201:28–35 (1992).
Conforti, et al., Modulation of Vitronectin Receptor Binding by Membrane Lipid Composition, The Journal of Biological Chemistry 265:4011–4019 (1990).
Danilov, et al., Phorbol Ester Modulation of Integrin-mediated Cell Adhesion: A Postreceptor Event, The Journal of Cell Biology 108:1925–1933 (1989).
Du, et al., Ligands "Activate" Integrin $\alpha_{IIb}\beta_3$ (Platelet GPIIb–IIIa), Cell 65:409–416 (1991).

Dustin, et al., Regulation of Locomotion and Cell–Cell Contact Area by the LFA-1 and ICAM-1 Adhesion Receptors, The Journal of Immunology 148:2654–2663 (1992).
Elices, et al., The human integrin VLA-2 is a collagen receptor on some cells and a collagen/laminin receptor on others, Proc. Natl. Acad. Sci. USA 86:9906–9910 (1989).
Faull, et al., Affinity Modulation of Integrin $\alpha_5\beta_1$: Regulation of the Functional Response by Soluble Fibronectin, The Journal of Cell Biology 121:155–162 (1993).
Frelinger, et al., Monoclonal Antibodies to Ligand-occupied Comformers of Integrin $\alpha_{IIb}\beta_3$ (Glycoprotein IIb–IIIa) Alter . . . The Journal of Biological Chemistry 266:17106–17111 (1991).
Frelinger, et al., Selective Inhibition of Integrin Function by Antibodies Specific for Ligand-occupied Receptor Conformers, The Journal of Biological Chemistry 265:6346–6352 (1990).
Gailit, et al., Regulation of the Fibronectin Receptor Affinity by Divalent Cations, The Journal of Biological Chemistry 263:12927–12932 (1988).
Ginsberg, et al., The Mechanism of Thrombin–Induced Platelet Factor 4 Secretion, Blood 55:661–668 (1980).
Ginsberg, et al., Inside–out Integrin signaling, Current Opinion in Cell Biology 4:766–771 (1992).
Grant, et al., Effects of Chymotrypsin on the Release Reaction and Aggregation of Blood Platelets, Proceedings of the Society for Experimental Biology and Medicine 165:114–117 (1980).
Hemler, VLA Proteins in the Integrin Family, Structures, Functions, and Their Role on Leukocytes, Annu. Rev. Immunol. 8:365–400 (1990).
Hermanowski–Vosatka, et al., Integrin Modulating Factor–1: A Lipid That Alters the Function of Leukocyte Integrins, Cell 68:341–352 (1992).
Hynes, Integrins: Versatility, Modulation, and Signaling in Cell Adhesion, Cell 69:11–25 (1992).
Hynes, et al., Integrin Heterodimer and Receptor Complexity in Avian and Mammalian Cells, The Journal of Cell Biology, 109:409–420 (1989).
Kirchhofer, et al., Cation-dependent Changes in the Binding Specificity of the Platelet Receptor GPIIb/IIIa, The Journal of Biological Chemistry 265:18525–18530 (1990).
Kovach, et al., A Monoclonal Antibody to $\beta_1$ Integrin (CD29) Stimulates VLA-dependent Adherence of Leukocytes to Human Umbilical Vein . . . The Journal of Cell Biology 116:499–509 (1992).

(List continued on next page.)

Primary Examiner—Garnette D. Draper
Assistant Examiner—Karen E. Brown
Attorney, Agent, or Firm—Fish & Richardson

[57] ABSTRACT

The invention features a method for inhibiting the ligand binding of an integrin in a cell involving introducing into the cell a compound which inhibits integrin activation, a method for identifying compounds which inhibit integrin activation, and chimeric integrin molecules.

9 Claims, 9 Drawing Sheets

OTHER PUBLICATIONS

Kunkel, Rapid and efficient site-specific mutagenesis without phenotypic selection, Proc. Natl. Acad. Sci. USA 82:488–492 (1985).

Loftus, et al., A $\beta_3$ Integrin Mutation Abolishes Ligand Binding and Alters Divalent Cation–Dependent Conformation, Science 249:915–918 (1990).

Masumoto et al, Multiple Activation States of VLA–4, The Journal of Biological Chemistry 268:228–234 (1993).

Munson, et al., Ligand: Versatile Computerized Approach for Characterization of Ligand–Binding Systems, Analytical Biochemistry 107:220–239 (1980).

Neugebauer, et al., Cell–surface regulation of $\beta_1$–integrin activity on developing retinal neurons, Nature 350:68–71 (1991).

O'Toole, et al., Modulation of the Affinity of Integrin $\alpha_{IIb}\beta_3$ GPIIb–IIIa) by the Cytoplasmic Domain of $\alpha_{IIb}$, Science 254:845–847 (1991).

O'Toole, et al., Affinity modulation of the $\alpha_{IIb}\beta_3$ integrin (platelet GPIIb–IIIa) is an intrinsic property of the receptor, Cell Regulation 1:883t14 893 (1990).

O'Toole, et al., Efficient Surface Expression of Platelet GPIIb–IIIa Requires Both Subunits, Blood 74:14–18 (1989).

Plow, et al., Related Binding Mechanisms for Fibrinogen, Fibronectin, von Willebrand Factor, and Thrombospondin on Thrombin–Stimulated Human Platelets, Blood 66:724–727 (1985).

Ruoslahti, Integrins, J. Clinical Investigation 87:1–5 (1991).

Smyth, et al., Fibrinogen Binding to Purified Platelet Glycoprotein IIb–IIIa (Integrin $\alpha_{IIb}\beta_3$ is Modulated by Lipids, The Journal of Biological Chemistry 267:15568–15577 (1992).

Springer, Adhesion receptors of the immune system, Nature 346:425–434 (1990).

Weitzman, et al., The Function and Distinctive Regulation of the Integrin VLA–3 in Cell Adhesion, Spreading, and Homotypic Cell Aggregation, The journal of Biological Chemistry 268:8651–8657 (1993).

Werb, et al., Signal Transduction through the Fibronectin Receptor Induces Collagenase and Stromelysin Gene Expression, The Journal of Cell Biology 109:877–889 (1989).

Ylänne, et al., Distinct Functions of Integrin $\alpha$ and $\beta$ Subunit Cytoplasmic Domains in Cell Spreading and Formation of Focal Adhesions, The Journal of Cell Biology 122:223–233 (1993).

Zucker, et al., Platelet Activation, Arteriosclerosis 5:2–18 (1985).

O'Toole et al, J. Cell Biol. 124 1047–1059 (1994).

Picker et al, Eur. J. Immunol. 23 2751–2757 (1993).

```
            989 991  996
       α_IIb KVGFFKRNRP PLEEDDEEGE                                    (SEQ ID NO: 1)
               ↑
       α_V   RMGFFKRVRP PQEEQEREQL QPHENGEGNS ET                      (SEQ ID NO: 2)

α_M   KLGFFKRQYK DMMSEGGPPG AEPQ                               (SEQ ID NO: 3)

α_L   KVGFFKRNLK EKMEAGRGVP NGIPAEDSEQ LASGQEAGDP GCLKPLHEKD SESGGGKD  (SEQ ID NO: 4)

α_Ra  KVDGIDKLDI EFLQPGGSTS SRGSW                              (SEQ ID NO: 5)

α_2   KLGFFKRKYE KMTKNPDEID ETTELSS                            (SEQ ID NO: 6)

α_5   KLGFFKRSLP YGTAMEKAQL KPPATSDA                           (SEQ ID NO: 7)

α_6A  KCGFFKRNKK DHYDATYHKA EIHAQPSDKE RLTSDA                  (SEQ ID NO: 8)

α_6B  KLGFFKRSRY DDSVPRYHAV RIRKEEREIK DEKYIDNLEK KQWITKWNRN ESYS  (SEQ ID NO: 9)

716      724  728                          P
       β_3  KLLITIHDRK EFAKFEEERA RAKWDTANNP LYKEATSTFT NITYRGT       (SEQ ID NO: 10)
                        ↑
       β_2  KALIHLSDLR EYRRFEKEKL KSQWNNDNPL FKSATTTVMN PKFAES        (SEQ ID NO: 11)

β_1  KLLMIIHDRR EFAKFEKEKM NAKWDTGENP IYKSAVTTVV NPKYEGK       (SEQ ID NO: 12)
```

FIG. 2

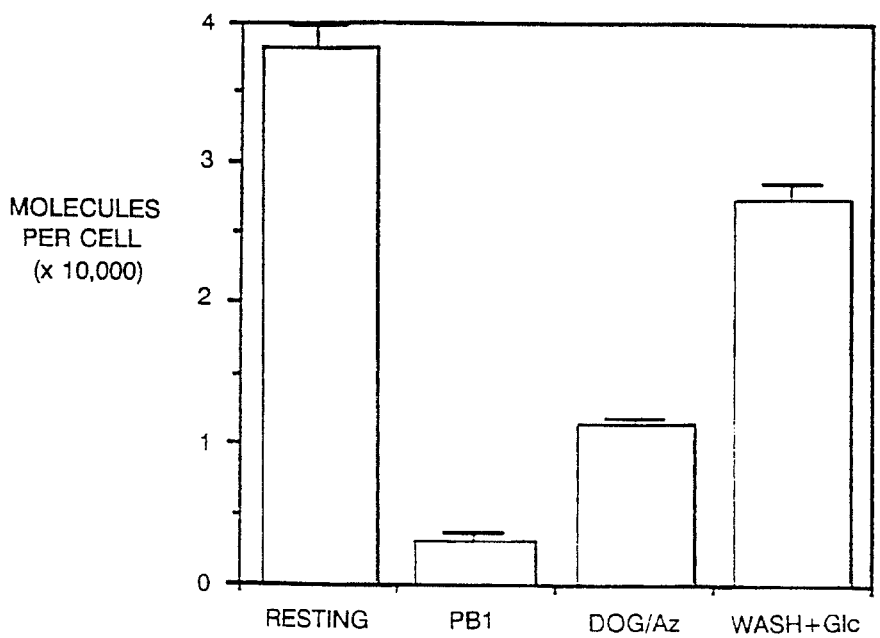

FIG. 1C

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:

(A) LENGTH: 20
(B) TYPE: amino acid
(C) STRANDEDNESS:
(D) TOPOLOGY: linear (xi) SEQUENCE DESCRIPTION: SEQ ID NO: 1:

Lys Val Gly Phe Phe Lys Arg Asn Arg Pro Pro Leu Glu Glu Asp Asp
1               5                   10                  15
Glu Glu Gly Glu
            20

(2) INFORMATION FOR SEQ ID NO: 2:

(i) SEQUENCE CHARACTERISTICS:
    (A) LENGTH: 32
    (B) TYPE: amino acid
    (C) STRANDEDNESS:
    (D) TOPOLOGY: linear (xi) SEQUENCE DESCRIPTION: SEQ ID NO: 2:

Arg Met Gly Phe Phe Lys Arg Val Arg Pro Pro Gln Glu Glu Gln Glu
1               5                   10                  15
Arg Glu Gln Leu Gln Pro His Glu Asn Gly Glu Gly Asn Ser Glu Thr
                20                  25                  30

(2) INFORMATION FOR SEQ ID NO: 3:

(i) SEQUENCE CHARACTERISTICS:
    (A) LENGTH: 24
    (B) TYPE: amino acid
    (C) STRANDEDNESS:
    (D) TOPOLOGY: linear (xi) SEQUENCE DESCRIPTION: SEQ ID NO: 3:

Lys Leu Gly Phe Phe Lys Arg Gln Tyr Lys Asp Met Met Ser Glu Gly
1               5                   10                  15
Gly Pro Pro Gly Ala Glu Pro Gln
            20

(2) INFORMATION FOR SEQ ID NO: 4:

(i) SEQUENCE CHARACTERISTICS:
    (A) LENGTH: 58
    (B) TYPE: amino acid
    (C) STRANDEDNESS:
    (D) TOPOLOGY: linear (xi) SEQUENCE DESCRIPTION: SEQ ID NO: 4:

Lys Val Gly Phe Phe Lys Arg Asn Leu Lys Glu Lys Met Glu Ala Gly
1               5                   10                  15
Arg Gly Val Pro Asn Gly Ile Pro Ala Glu Asp Ser Glu Gln Leu Ala
                20                  25                  30
Ser Gly Gln Glu Ala Gly Asp Pro Gly Cys Leu Lys Pro Leu His Glu
                35                  40                  45
Lys Asp Ser Glu Ser Gly Gly Gly Lys Asp
        50                  55

(2) INFORMATION FOR SEQ ID NO: 5:

(i) SEQUENCE CHARACTERISTICS:
    (A) LENGTH: 25
    (B) TYPE: amino acid
    (C) STRANDEDNESS:
    (D) TOPOLOGY: linear (xi) SEQUENCE DESCRIPTION: SEQ ID NO: 5:

Lys Val Asp Gly Ile Asp Lys Leu Asp Ile Glu Phe Leu Gln Pro Gly
1               5                   10                  15

Gly Ser Thr Ser Ser Arg Gly Ser Trp
            20                  25

( 2 ) INFORMATION FOR SEQ ID NO: 6:

( i ) SEQUENCE CHARACTERISTICS:
        ( A ) LENGTH: 27
        ( B ) TYPE: amino acid
        ( C ) STRANDEDNESS:
        ( D ) TOPOLOGY: linear ( x i ) SEQUENCE DESCRIPTION: SEQ ID NO: 6:

Lys Leu Gly Phe Phe Lys Arg Lys Tyr Glu Lys Met Thr Lys Asn Pro
1               5                   10                  15

Asp Glu Ile Asp Glu Thr Thr Glu Leu Ser Ser
            20                  25

( 2 ) INFORMATION FOR SEQ ID NO: 7:

( i ) SEQUENCE CHARACTERISTICS:
        ( A ) LENGTH: 28
        ( B ) TYPE: amino acid
        ( C ) STRANDEDNESS:
        ( D ) TOPOLOGY: linear ( x i ) SEQUENCE DESCRIPTION: SEQ ID NO: 7:

Lys Leu Gly Phe Phe Lys Arg Ser Leu Pro Tyr Gly Thr Ala Met Glu
1               5                   10                  15

Lys Ala Gln Leu Lys Pro Pro Ala Thr Ser Asp Ala
            20                  25

( 2 ) INFORMATION FOR SEQ ID NO: 8:

( i ) SEQUENCE CHARACTERISTICS:
        ( A ) LENGTH: 36
        ( B ) TYPE: amino acid
        ( C ) STRANDEDNESS:
        ( D ) TOPOLOGY: linear ( x i ) SEQUENCE DESCRIPTION: SEQ ID NO: 8:

Lys Cys Gly Phe Phe Lys Arg Asn Lys Lys Asp His Tyr Asp Ala Thr
1               5                   10                  15

Tyr His Lys Ala Glu Ile His Ala Gln Pro Ser Asp Lys Glu Arg Leu
            20                  25                  30

Thr Ser Asp Ala
        35

( 2 ) INFORMATION FOR SEQ ID NO: 9:

( i ) SEQUENCE CHARACTERISTICS:
        ( A ) LENGTH: 54
        ( B ) TYPE: amino acid
        ( C ) STRANDEDNESS:
        ( D ) TOPOLOGY: linear ( x i ) SEQUENCE DESCRIPTION: SEQ ID NO: 9:

Lys Leu Gly Phe Phe Lys Arg Ser Arg Tyr Asp Asp Ser Val Pro Arg
1               5                   10                  15

Tyr His Ala Val Arg Ile Arg Lys Glu Glu Arg Glu Ile Lys Asp Glu
            20                  25                  30

Lys Tyr Ile Asp Asn Leu Glu Lys Lys Gln Trp Ile Thr Lys Trp Asn
            35                  40                  45

Arg Asn Glu Ser Tyr Ser
            50

(2) INFORMATION FOR SEQ ID NO: 10:

(i) SEQUENCE CHARACTERISTICS:
        (A) LENGTH: 47
        (B) TYPE: amino acid
        (C) STRANDEDNESS:
        (D) TOPOLOGY: linear (xi) SEQUENCE DESCRIPTION: SEQ ID NO: 10:

Lys Leu Leu Ile Thr Ile His Asp Arg Lys Glu Phe Ala Lys Phe Glu
 1           5                   10                  15

Glu Glu Arg Ala Arg Ala Lys Trp Asp Thr Ala Asn Asn Pro Leu Tyr
            20                  25                  30

Lys Glu Ala Thr Ser Thr Phe Thr Asn Ile Thr Tyr Arg Gly Thr
            35                  40                  45

(2) INFORMATION FOR SEQ ID NO: 11:

(i) SEQUENCE CHARACTERISTICS:
        (A) LENGTH: 46
        (B) TYPE: amino acid
        (C) STRANDEDNESS:
        (D) TOPOLOGY: linear (xi) SEQUENCE DESCRIPTION: SEQ ID NO: 11:

Lys Ala Leu Ile His Leu Ser Asp Leu Arg Glu Tyr Arg Arg Phe Glu
 1           5                   10                  15

Lys Glu Lys Leu Lys Ser Gln Trp Asn Asn Asp Asn Pro Leu Phe Lys
            20                  25                  30

Ser Ala Thr Thr Thr Val Met Asn Pro Lys Phe Ala Glu Ser
            35                  40                  45

(2) INFORMATION FOR SEQ ID NO: 12:

(i) SEQUENCE CHARACTERISTICS:
        (A) LENGTH: 47
        (B) TYPE: amino acid
        (C) STRANDEDNESS:
        (D) TOPOLOGY: linear (xi) SEQUENCE DESCRIPTION: SEQ ID NO: 12:

Lys Leu Leu Met Ile Ile His Asp Arg Arg Glu Phe Ala Lys Phe Glu
 1           5                   10                  15

Lys Glu Lys Met Asn Ala Lys Trp Asp Thr Gly Glu Asn Pro Ile Tyr
            20                  25                  30

Lys Ser Ala Val Thr Thr Val Val Asn Pro Lys Tyr Glu Gly Lys
            35                  40                  45

(2) INFORMATION FOR SEQ ID NO: 13:

(i) SEQUENCE CHARACTERISTICS:
        (A) LENGTH: 6
        (B) TYPE: amino acid
        (C) STRANDEDNESS:
        (D) TOPOLOGY: linear (xi) SEQUENCE DESCRIPTION: SEQ ID NO: 13:

Gly Arg Gly Asp Ser Pro
 1           5

(2) INFORMATION FOR SEQ ID NO: 14:

( i ) SEQUENCE CHARACTERISTICS:
    ( A ) LENGTH: 5
    ( B ) TYPE: amino acid
    ( C ) STRANDEDNESS:
    ( D ) TOPOLOGY: linear ( x i ) SEQUENCE DESCRIPTION: SEQ ID NO: 14:

Gly Phe Phe Lys Arg
 1               5

( 2 ) INFORMATION FOR SEQ ID NO: 15:

( i ) SEQUENCE CHARACTERISTICS:
        ( A ) LENGTH: 5
        ( B ) TYPE: amino acid
        ( C ) STRANDEDNESS:
        ( D ) TOPOLOGY: linear ( x i ) SEQUENCE DESCRIPTION: SEQ ID NO: 15:

Leu Gly Phe Phe Lys
 1               5

( 2 ) INFORMATION FOR SEQ ID NO: 16:

( i ) SEQUENCE CHARACTERISTICS:
        ( A ) LENGTH: 5
        ( B ) TYPE: amino acid
        ( C ) STRANDEDNESS:
        ( D ) TOPOLOGY: linear ( x i ) SEQUENCE DESCRIPTION: SEQ ID NO: 16:

Val Gly Phe Phe Lys
 1               5

( 2 ) INFORMATION FOR SEQ ID NO: 17:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( x i ) SEQUENCE DESCRIPTION: SEQ ID NO: 17:

CGGGCCTTGG AGGAGAGGGC CATTC                                    25

( 2 ) INFORMATION FOR SEQ ID NO: 18:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 18:

CTCTGTTGGG AGGGAAACGA                                          20

( 2 ) INFORMATION FOR SEQ ID NO: 19:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 19:

TGTAAACAAG GGTCCTTCAC                                          20

METHODS FOR IDENTIFYING INHIBITORS OF INTEGRIN ACTIVATION

This invention was supported in part by the U.S. Government under grant numbers HL48728, HL28235, and AR27214 awarded by the National Institute of Health. The Government has certain rights in the invention.

BACKGROUND OF THE INVENTION

Cells alter their adhesiveness in response to developmental events and environmental cues. These adaptations are often mediated through integrins, adhesion receptors composed of two transmembrane subunits, α and β (Hynes, Cell 69:11–25, 1992). Rapid changes in integrin function are critical in cell migration, cellular aggregation, and leukocyte transmigration during inflammation (Hynes, Cell 69:11–25, 1992; Albelda and Buck, FASEB 4:2868–2880, 1990; Hemler, Annu. Rev. Immunol. 8:365–400, 1990; Dustin et al., J. Immunol. 148:2654–2663, 1992; Springer, Nature 346:425–434, 1990; Ginsberg et al., Curr. Opin. Cell Biol. 4:766–771, 1992; Ruoslahti, J. Clin. Invest. 87:1–5, 1991). A given integrin may also manifest varying adhesive competence depending on its cellular environment (Chan and Hemler, J. Cell. Biol. 120:537–543, 1993; Masumoto and Hemler, J. Biol. Chem. 268:228–234, 1993; Weitzman et al., J. Biolo Chem. 268:8651–8657, 1993; Elices and Hemler, Proc. Natl. Acad. Sci. USA 86:9906–9910, 1989; Kirchofer et al., J. Biol. Chem. 265:18525–18530, 1990), or the state of differentiation of the cell in which it is expressed (Haimovich et al., Cell Regulation 2:271–283, 1991; Neugebauer and Reichardt, Nature 350:68–71, 1991; Adams and Watt, Cell 63:425–435, 1990; Chan and Hemler, J. Cell Biol. 120:537–543, 1993). Such variations in function may be due to changes in ligand binding affinity as occurs with certain $\beta_3$ (Bennett and Vilaire, J. Clin. Invest. 64:1393–1401, 1979), $\beta_2$ (Altieri et al., J. Cell Biol. 107:1893–1900, 1988), and $\beta_1$ (Faull et al., J. Cell Biol. 121:155–162, 1993) integrins. Changes in adhesive function may also occur without changes in ligand binding affinity. For example, phorbol esters stimulate the $\alpha_5\beta_1$-dependent adhesion of Chinese Hamster ovary cells (Danilov and Juliano, J. Cell. Biol. 108:1925–1933, 1989) to fibronectin (Fn) with no change in Fn binding affinity. Similarly, certain $\beta_3$ mutations reduce $\alpha_{IIb}\beta_3$-dependent cell adhesion to fibrinogen (Fg) without changing Fg binding affinity (Ylanne et al., J. Cell Biol. 122:223–233, 1993). Such affinity-independent changes in integrin function are ascribed to "post receptor occupancy events" (Danilov and Juliano, J. Cell. Biol. 108:1925–1933, 1989). Nevertheless, the host cell governs the capacity of solubilized recombinant $\alpha_2\beta_1$ to bind to collagen sepharose (Chan and Hemler, J. Cell. Biol. 120:537–543, 1993). This last result suggests that some cell type-specific differences in integrin function may be due to differences in ligand binding affinity.

A variety of in vitro treatments may alter integrin affinity. When purified $\alpha_{IIb}\beta_3$ is pretreated with RGD peptides, it subsequently binds Fg and PAC1 (Du et al., Cell 65:409–416, 1991; Smyth et al., J. Biol. Chem. 267:15568–15577, 1992). Certain anti-$\beta_3$ antibodies directly increase the Fg binding affinity of $\alpha_{IIb}\beta_3$ (Frelinger et al., J. Biol. Chem. 266:17106–17111, 1991) and certain anti-$\beta_1$ antibodies activate $\alpha_5\beta_1$ to bind Fn with high affinity (Faull et al., J. Cell Biolo 121:155–162, 1993). Changes in the divalent cation composition of the extracellular medium, proteolytic digestion, and treatment with reducing agents may also "activate" integrins (Kirchofer et al., J. Biol. Chem. 265:18525–18530, 1990; Gailit and Ruoslahti, J. Biol. Chem. 263:12927–12932, 1988; Altieri, J. Immunol. 147:1891–1898, 1991; Masumoto and Hemler, J. Biol. Chem. 268:228–234, 1993; Weitzman et al., J. Biol. Chem. 268:8651–8657, 1993; Zucker and Nachmias, Arteriosclerosis 5:2–18, 1985; Grant and Zucker, Proc. Soc. Exp. Biol. Med. 165:114–117, 1980). Thus, moieties that interact with the extracellular domain can modulate integrin affinity. Furthermore, lipid environment can alter the ligand binding capacity of an integrin (Smyth et al., J. Biol. Chem. 267:15568–15577, 1992; Conforti et al., J. Biol. Chem. 265:4011–4019, 1990) and an apparently novel lipid, IMF-1, may regulate $\alpha_M\beta_2$ (Hermanowski-Vosatka et al., Cell 68:341–352, 1992). Although many treatments may change integrin affinity in vitro, the mechanism(s) of physiological modulation has not been defined.

SUMMARY OF THE INVENTION

We have shown that the cytoplasmic domain of integrin molecules is involved in modulating the ligand binding activity of the integrin extracellular domain.

Accordingly, the invention features, in one aspect, a method for measuring the ability of a candidate compound to inhibit activation of a target integrin. In this method, a cell expressing a chimeric integrin is cultured in the presence of the candidate compound. The cell is then contacted with a ligand that binds to the reporter integrin only when the reporter integrin is activated. The level of ligand bound to the chimeric integrin in the presence of the candidate compound is a measure of the ability of the candidate compound to inhibit activation of the target integrin. In a preferred embodiment, the reporter integrin is $\alpha_{IIb}\beta_3$. In another preferred embodiment, the target integrin is selected from the group consisting of $\alpha_v \neq_3$, $\alpha_M\beta_2$, $\alpha_L\beta_2$, $\alpha_2\beta_1$, $\alpha_5\beta_1$, $\alpha_{6A}\beta_1$, $\alpha_{6B}\beta_1$, $\alpha_{IIb}\beta_3$, and $\alpha_4\beta_1$.

"Integrin activation" as used herein, is defined as the process whereby the cytoplasmic domain of the integrin stimulates the ligand binding activity of the extracellular domain.

A "chimeric integrin", as used herein, is defined as an integrin comprising the extracellular and transmembrane domains from a reporter integrin and the cytoplasmic domain from a target integrin. Accordingly, "reporter integrin" is defined as an integrin from which the extracellular and transmembrane domains of a chimeric integrin are derived, while "target integrin" is defined as an integrin from which the cytoplasmic domain of a chimeric integrin is derived.

The ligand used in the screening method of the invention can be any molecule, e.g., an antibody, that binds to the reporter integrin only when the reporter is activated. In the case of the $\alpha_{IIb}\beta_3$ reporter integrin, the ligand is preferably the PAC1 antibody or fibrinogen.

The cell used in the screening method of the invention is preferably one in which the target integrin is naturally expressed and activated. Cell types that can be used in the invention include, but are not limited to, leukocytes, fibroblasts, and cancer cells. Specific examples of useful cells include: Jurkat (e.g., Jurkat clone E6-1, which can be obtained from the American Type Culture Collection, Rockville, Md.; ATCC TIB 152), K562 (human erythroleukemia cells; ATCC CCL 243), CHO (Chinese Hamster Ovary cells; ATCC CCL 61), THP-1 (human monocytes; ATCC TIB 202), U937 (human histiocytic lymphoma cells; ATCC CRL 1593), WI-38 (human lung fibroblasts; ATCC CCL 75), and MG63 (human osteosarcoma cells; ATCC CRL 1427) cells. In addition, peripheral blood T cells and blood platelets, both of which can be isolated by standard methods, can be used in the invention.

In another aspect, the invention features a chimeric integrin molecule, as defined above. Any integrin can be used as a reporter and/or a target integrin. In a preferred embodiment, the reporter integrin is $\alpha_{IIb}\beta_3$. Preferred target integrins include, but are not limited to $\alpha_v\beta_3$, $\alpha_M\beta_2$, $\alpha_L\beta_2$, $\alpha_2\beta_1$, $\alpha_5\beta_1$, $\alpha_{6A}\beta_1$, $\alpha_{6B}\beta_1$, $\alpha_{IIb}\beta_3$, and $\alpha_4\beta_1$.

The invention also features a method of inhibiting the ligand binding activity of an integrin molecule in a cell involving introducing into the cell a compound which inhibits integrin activation. Preferably, the compound used to inhibit integrin activation is a small organic molecule, and the cell in which the compound inhibits integrin activation is a leukocyte, a platelet, or a cancer cell.

The inhibitors of the invention can be used to treat mammals, such as humans, who have or are at risk of developing an unwanted immune response, e.g., inflammation, or an immune response resulting from autoimmune disease or the presence of a transplanted organ or tissue. In addition, the inhibitors can be used to treat patients who have, or are at risk of developing cancer, as well as to treat patients who have, or are at risk of developing a thrombus.

The invention provides a rapid and facile method for identifying inhibitors of integrin activation in which a large number of compounds can be screened. The use of chimeric integrins allows inhibitors for target integrins to be identified even in cases in where an activation-specific ligand for the target integrin has not been identified. $\alpha_{IIb}\beta_3$ is a particularly useful reporter integrin, as the activation-specific ligands for $\alpha_{IIb}\beta_3$, PAC1 and Fg, do not bind to other commonly expressed tissue integrins.

Other features and advantages of the invention will become apparent from the following detailed description, and from the claims.

DETAILED DESCRIPTION

The drawings are first described.
Drawings

Figure 1A:
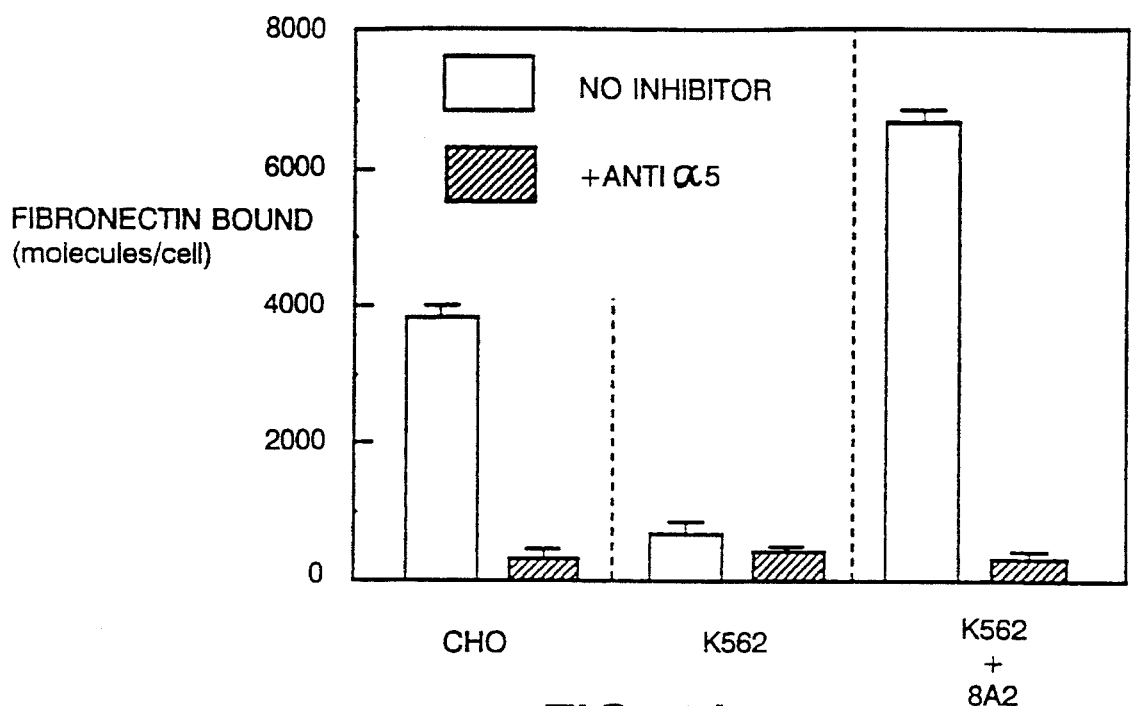
FIG. 1A is a graph showing the levels of fibronectin bound to CHO cells, K562 cells, and K562 cells in the presence of the "activating" antibody 8A2. The graph also shows the levels of fibronectin bound to the above-listed cells in the presence of an anti-$\alpha_5$ antibody.

FIG 1C is a graph showing the levels of fibronectin bound to resting CHO cells; CHO cells in the presence of the anti-$\alpha_5$ antibody (PB1); CHO cells incubated with deoxyglucose and sodium azide (DOG/Az); and CHO cells washed free of deoxyglucose and sodium azide, and returned to glucose medium (Wash+Glc).

FIG. 2 is a listing of the amino acid sequences (SEQ ID NOs: 1–12) of wild type and variant integrin cytoplasmic domains.

Figure 3B:
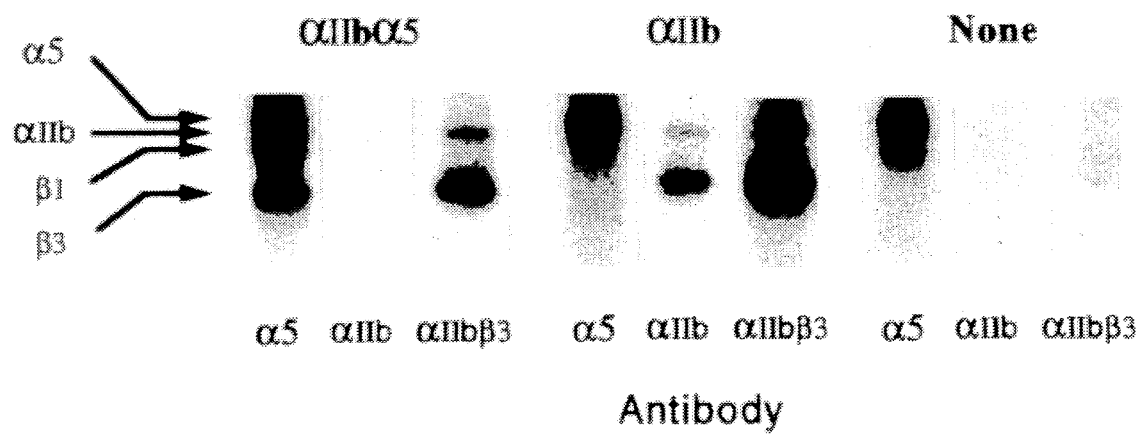
Figure 3C:
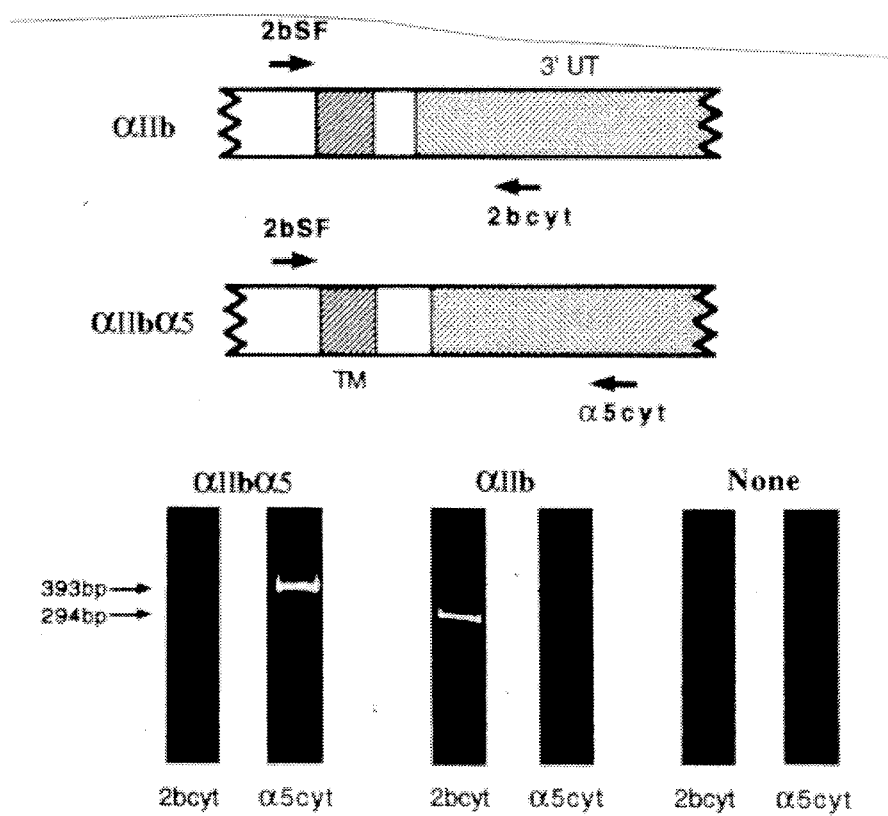
Figure 3A:
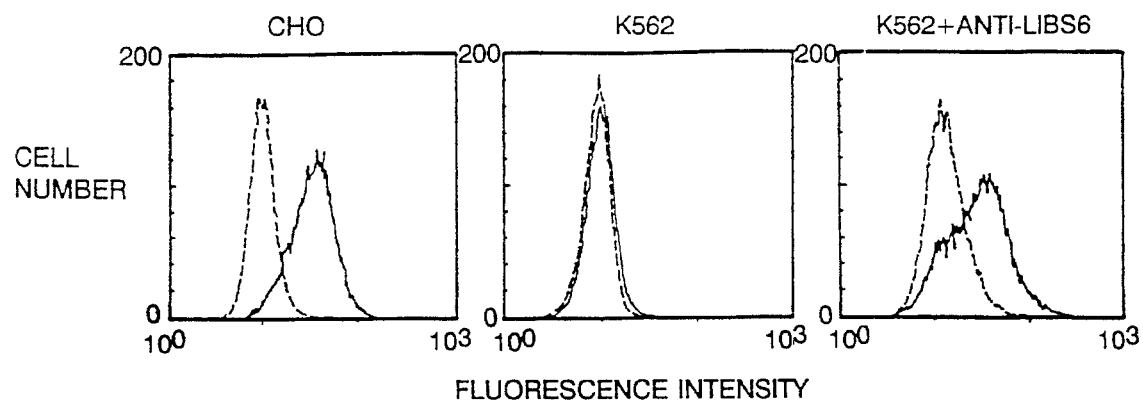

FIG. 3A is a graph of results from flow cytometry analysis of CHO and K562 cells stably transfected with chimeric integrins containing the cytoplasmic domains of α5 and $\beta_1$ and the extracellular domains of $\alpha_{IIb}$ and $\beta_3$.

FIG. 3B is an autoradiogram of immunoprecipitates of lysates prepared from surface iodinated wild type K562 cells (None) or stable K562 transfectants expressing the α subunit indicated at the tops of the lanes ($\alpha_{IIb}\alpha_5=\alpha_5$ cytoplasmic domain chimera), fractionated by SDS-PAGE. The immunoprecipitations were carried out with antibodies specific for the specific integrin domains indicated below each of the lanes.

FIG. 3C is an illustration of the locations of the 2bsf, 2bcyt and $\alpha_5$cyt primers used for PCR analysis. The transmembrane (TM: crosshatched), 3' untranslated (3'UT:stippled), and cytoplasmic and extracellular domain (clear) sequences are indicated. Also shown is a photograph of an agarose gel upon which amplified products were fractionated, with arrows indicating the positions of the 393 and 294 bp bands. The transfectant type is listed above, while the 3' primer used is indicated below.

Figure 4A:
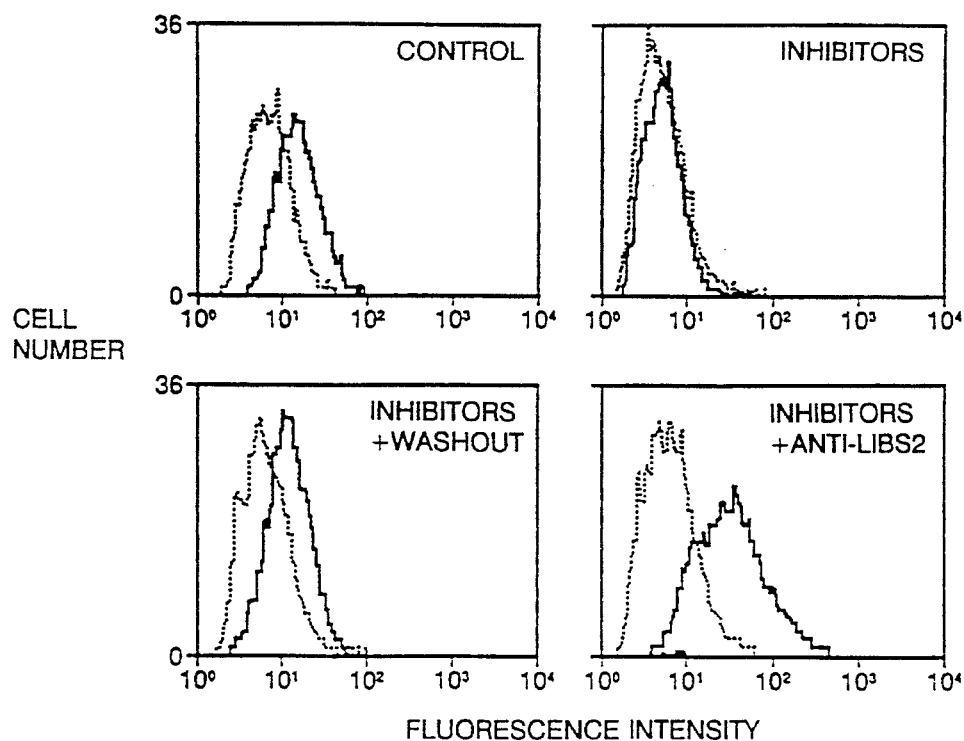

FIG. 4A is a graph of results from flow cytometry analysis of PAC1 binding to stable CHO transfectants expressing the $\alpha_5$ and $\alpha_1$ cytoplasmic domain chimeras in the absence (solid line) and presence (dotted line) of 2 mM GRGDSP (SEQ ID NO: 13) (Inhibitors: deoxyglucose+NAN$_3$).

Figure 4B:
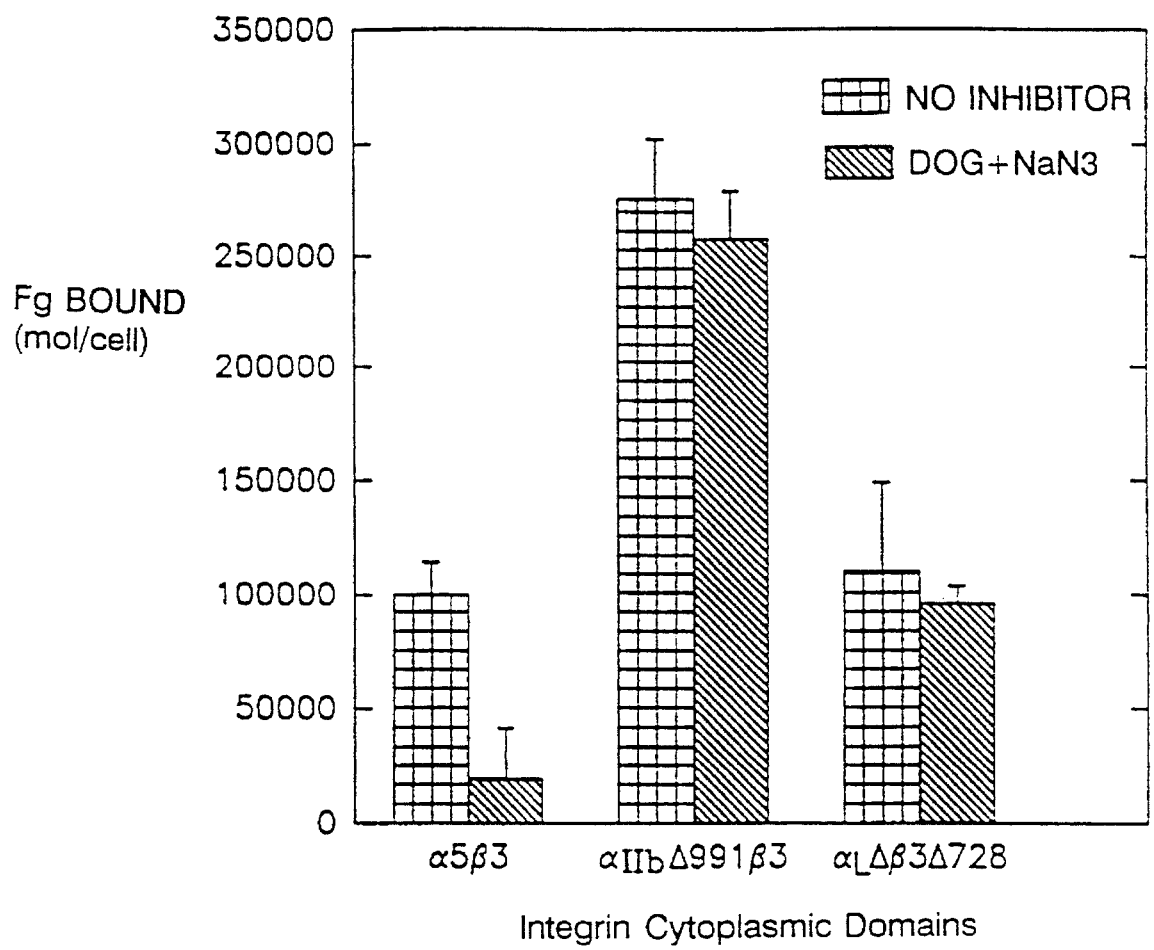

FIG. 4B is a graph showing the levels of Fg bound to stable CHO transfectants expressing the cytoplasmic domains indicated below the graph.

Figure 5A:
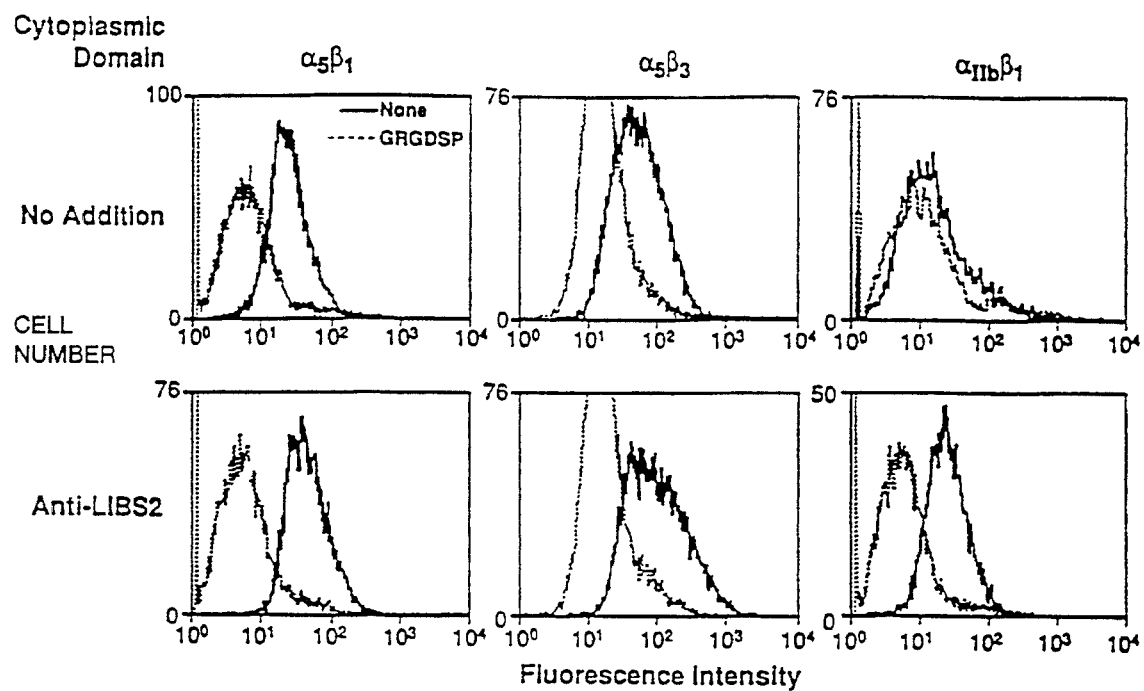

FIG. 5A is a graph of results from flow cytometry analysis of PAC1 binding to CHO cells transiently transfected with subunits comprised of the extracellular and transmembrane domains of $\alpha_{IIb}$ and $\beta_3$ joined to the indicated cytoplasmic domains. Binding was analyzed in the absence (solid line) or presence (dotted line) of GRGDSP (SEQ ID NO: 13) peptide.

Figure 5B:
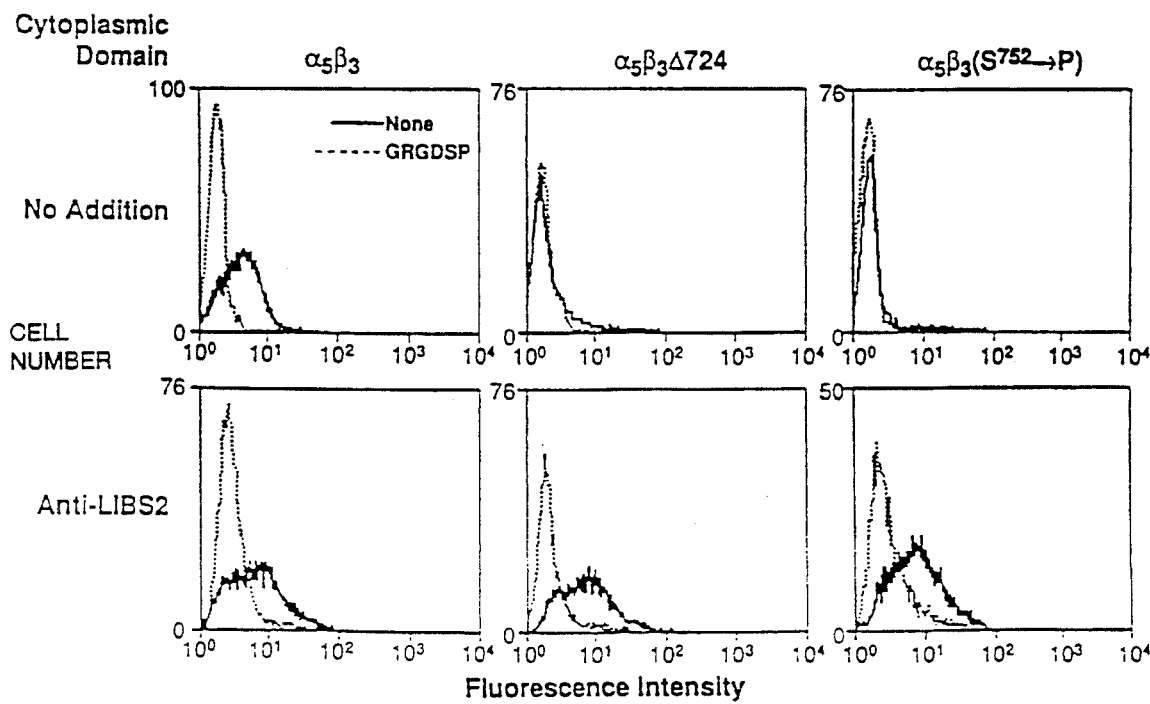

FIG. 5B is a graph of results from flow cytometry analysis of PAC1 binding to CHO cells CHO cell lines stably expressing recombinant $\alpha_{IIb}\beta_3$ chimeras containing the indicated cytoplasmic domains. Binding was analyzed in the absence (solid line) or presence (dotted line) of GRGDSP (SEQ ID NO: 13) peptide.

Figure 6A:
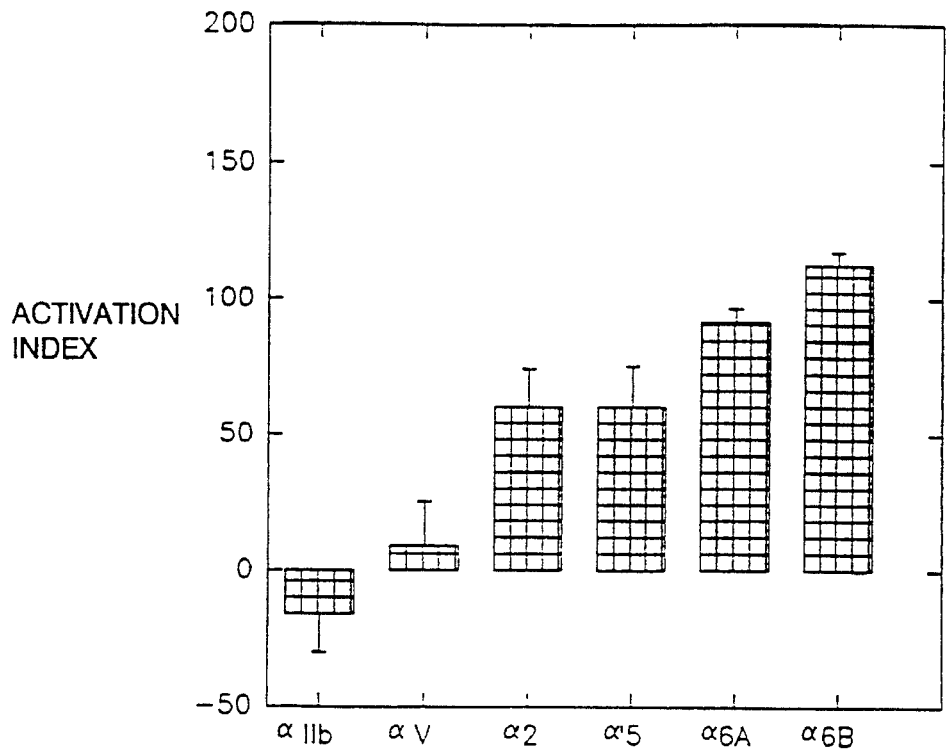

FIG. 6A is a graph showing the activation index for CHO cells transiently transfected with chimeric α subunits consisting of extracellular and transmembrane $\alpha_{IIb}$ with the indicated cytoplasmic domains, and $\beta_3$.

Figure 6B:
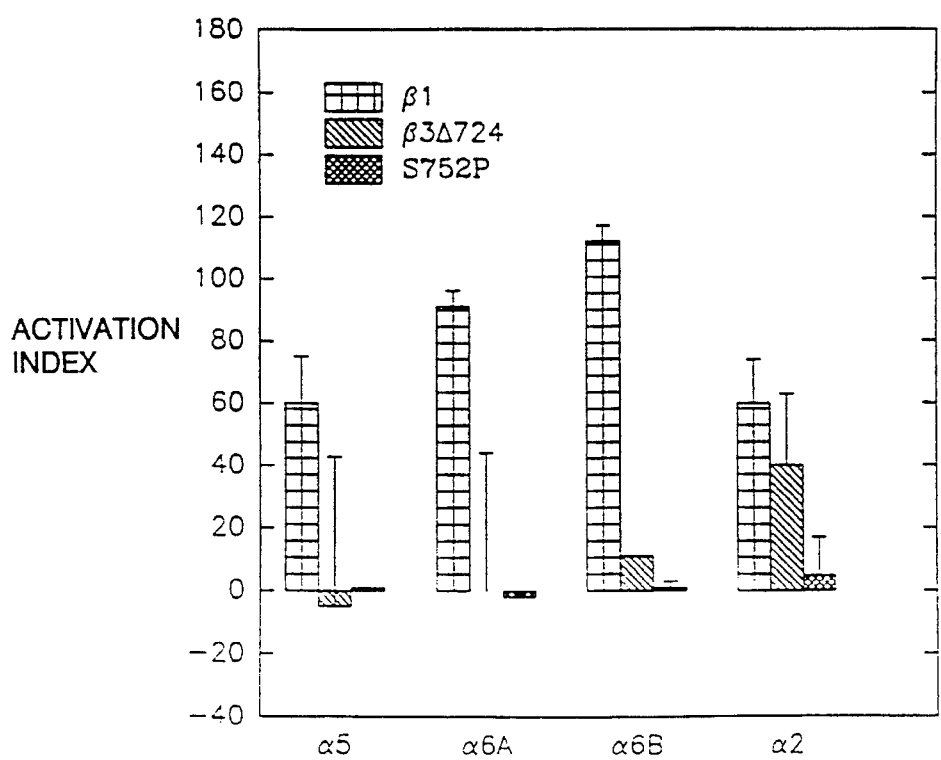

FIG. 6B is a graph showing the activation index for CHO cells transiently transfected with chimeric α subunits containing the indicated cytoplasmic sequences and a $\beta_3$ subunit in which the cytoplasmic domain was truncated ($\beta_3\Delta724$), contained the $S^{752}\rightarrow P$ mutation (S752P), or had been exchanged for the homologous region of $\beta_1$.

Figure 7A:
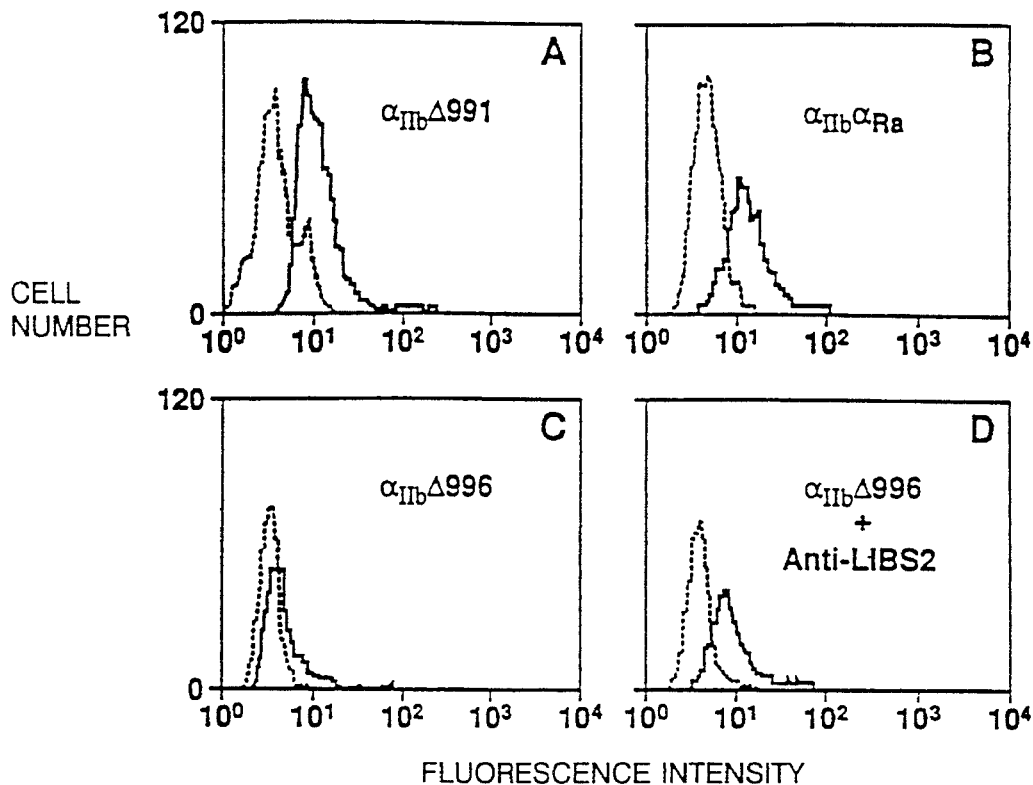

FIG. 7A is a series of graphs of the results of flow cytometry analysis of PAC1 binding to stable CHO cell lines co-transfected with $\alpha_{IIb}$ containing the indicated α cytoplasmic domain with wild type $\beta_3$.

Figure 7B:
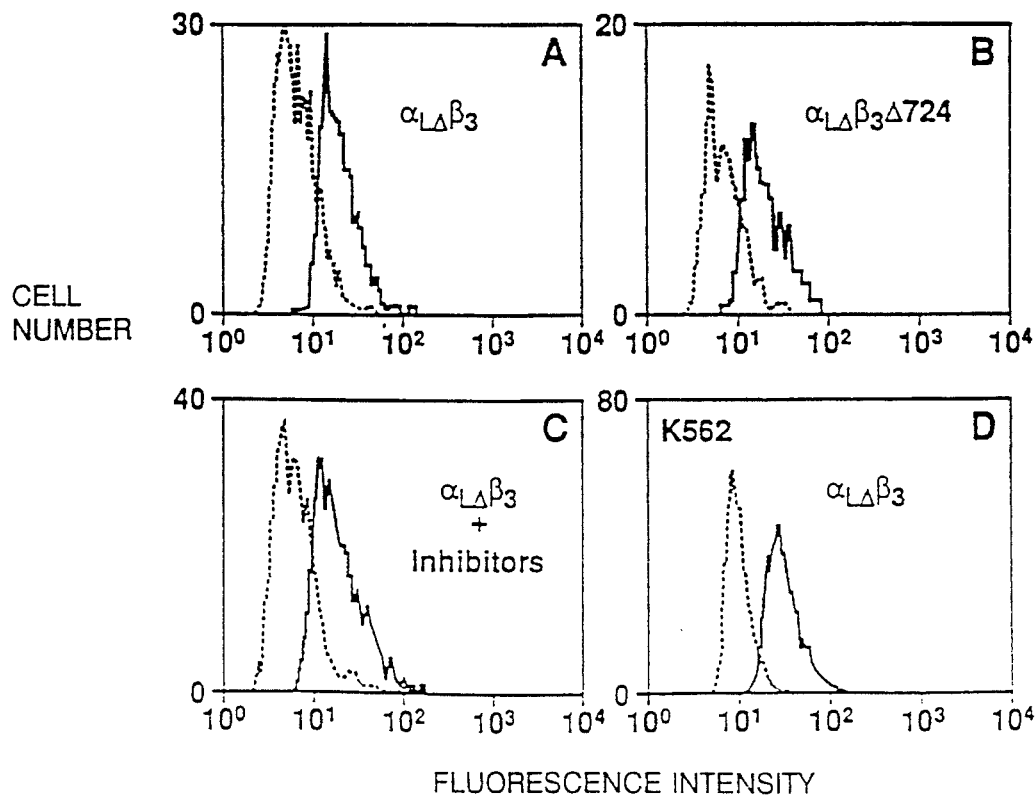

FIG. 7B is a series of graphs of the results of flow cytometry analysis of PAC1 binding to CHO cells transiently transfected with chimeras of the extracellular and transmembrane domains of $\alpha_{IIb}\beta_3$ joined to the indicated cytoplasmic domains.

Figure 8:
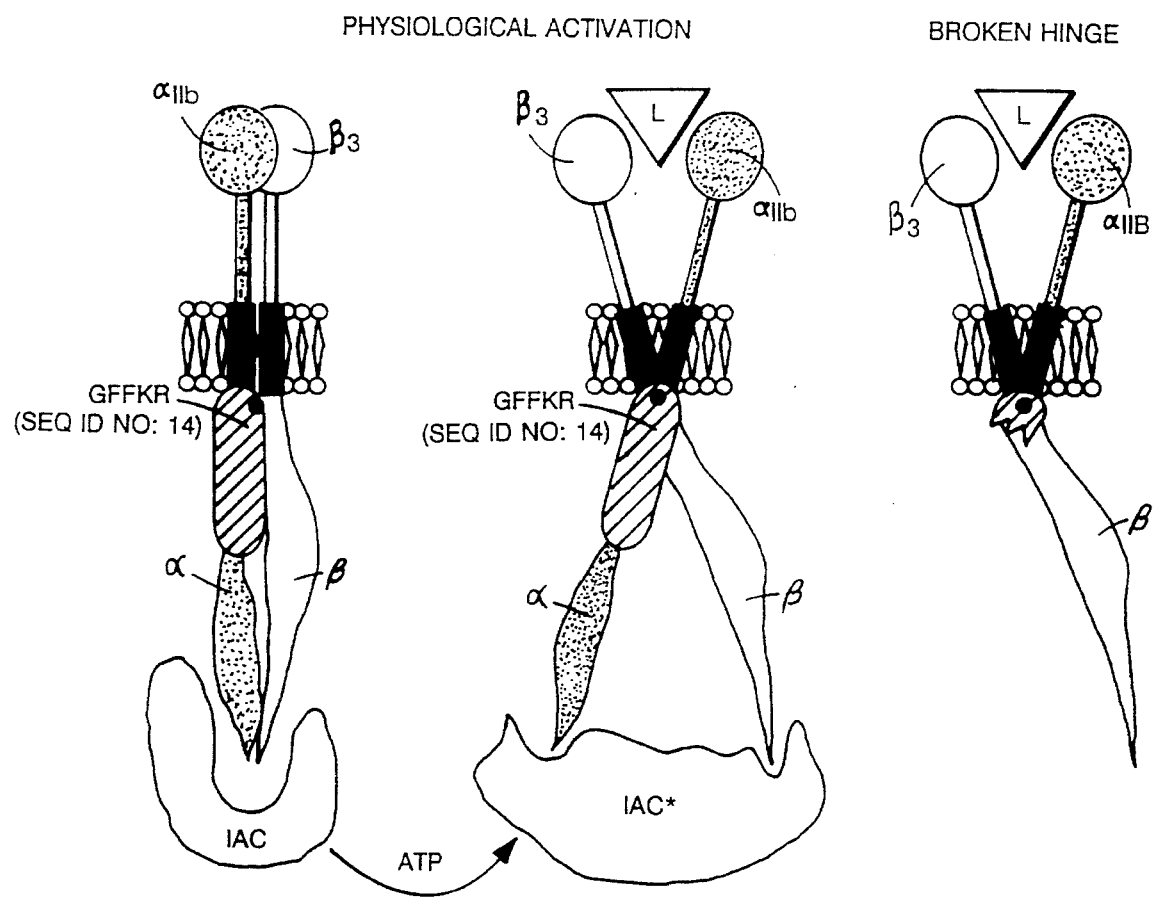

FIG. 8 is an illustration of a model for affinity modulation of integrins.

INHIBITORS

We have shown that the integrin cytoplasmic domain plays a role in activating the ligand binding activity of the integrin extracellular domain. Integrin-ligand binding interactions play central roles in a number of physiological processes, including activation of the immune response, inflammation, hemostasis, thrombosis, cell migration, and tumor cell invasion. Thus, inhibiting integrin activation can be useful in modulating these processes.

Inhibition of the ligand binding activity of an integrin can be achieved by administering a compound that inhibits integrin activation. Such a compound can be identified by methods ranging from rational drug design to screening of random compounds. The latter method is preferable, as a simple and rapid assay for carrying out this method is available. Small organic molecules are desirable candidate compounds for this analysis as frequently these molecules are capable of passing through the plasma membrane so that they can potentially act on integrin cytoplasmic domains.

The screening of small, membrane-permeable organic molecules for the ability to inhibit integrin activation is carried out as follows. First, compounds are tested in cultured cells expressing chimeric integrin molecules. Second, compounds which test positive in the cultured cells are tested in an animal model system.

Chimeric integrin molecules used in the cell culture-based screening method contain the extracellular and transmembrane domains of a reporter integrin fused to the intracellular domain of a target integrin. The preferred reporter integrin of the invention is $\alpha_{IIb}\beta_3$, as its known ligands, PAC1 (Shattil et al., J. Biol. Chem. 260:11107–11114, 1985) and Fg, bind specifically to activated $\alpha_{IIb}\beta_3$, and not to inactive $\alpha_{IIb}\beta_3$, or other integrins. Other integrins may also be used as reporter integrins in the invention, provided that an activation-specific ligand is available. Preferred target integrins include, but are not limited to $\alpha_v\beta_3$, $\alpha_M\beta_2$, $\alpha_L\beta_2$, $\alpha_2\beta_1$, $\alpha_5\beta_1$, $\alpha_{6A}\beta_1$, $\alpha_{6B}\beta_1$, $\alpha_{IIb}\beta_3$ and $\alpha_4\beta_1$. Chimeric integrins can be generated using standard methods of molecular biology (Sambrook et al., Molecular Cloning: A Laboratory Manual, 2nd, Cold Spring Harbor Laboratory Press, 1989).

The cell culture assay for identifying inhibitors of integrin activation involves culturing cells expressing a chimeric integrin in the presence or absence of a candidate compound, and determining the level of reporter integrin activation by contacting the cell with a ligand that binds to the reporter integrin only when the reporter integrin is activated. A compound tests positive in the cell culture assay if the amount of ligand bound to the reporter integrin in the presence of the compound is less than the amount bound in its absence.

Any reagent that binds to a reporter integrin specifically when it is activated, e.g., an activation-specific antibody, can be used as the ligand in the screening method of the invention. In the case of the $\alpha_{IIb}\beta_3$ reporter integrin, PAC1 and Fg are preferable ligands. The ligand can be tagged with a label, e.g., an enzymatic, chromogenic, radioactive, or luminescent label, which can be detected using standard methods in the art, including flow cytometry, direct radioligand binding assays, and ELISA. Binding of the ligand to the reporter integrin can also be detected by the use of antibodies which specifically bind to the ligand which can be detected by standard methods.

Compounds found to affect integrin activation in the cell culture assay can be further tested in animal model systems. A candidate compound can be administered to an appropriate animal, e.g., an immunocompetent mouse which has a non-MHC matched skin graft, and the effect of the compound can be determined by monitoring the immune response of the mouse.

Role of Cytoplasmic Tail in Integrin Activation

Cell type-specific and energy-dependent affinity modulation of integrin $\alpha_5\beta_1$.

Figure 1B:
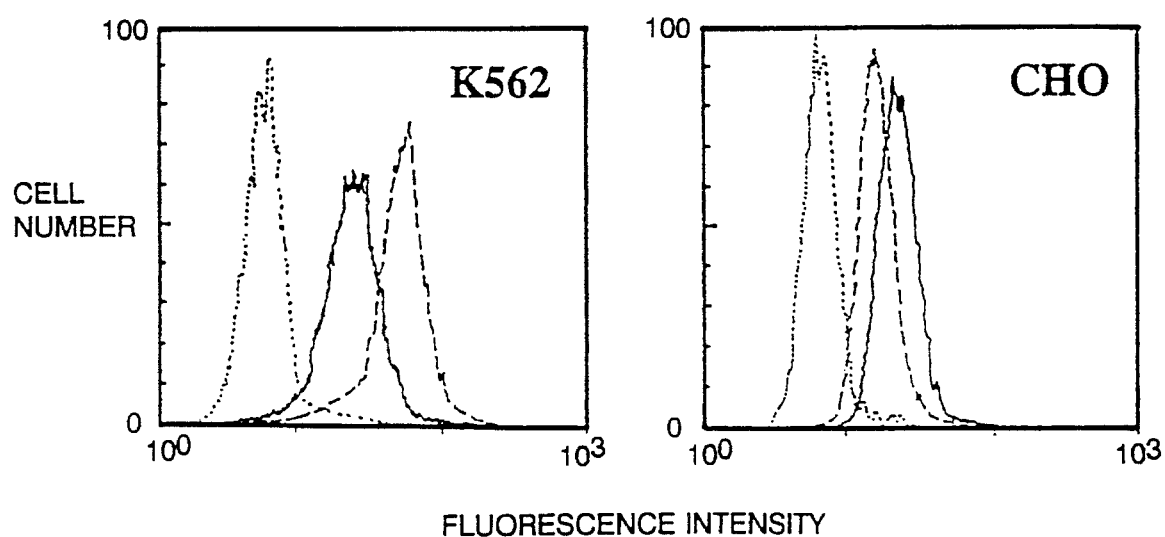
FIG. 1B is a graph of results from flow cytometry analysis of K562 and CHO cells stained with an irrelevant mouse IgG (dotted line), an anti-$\beta_1$ antibody (solid line), and an anti-$\alpha_5$ antibody (dashed line).

There is evidence for cell type-specific control of the adhesive function of integrins. To begin to investigate the cell type-specific control of ligand binding affinity, we analyzed the binding of soluble fibronectin (Fn) to cells expressing integrin $\alpha_5\beta_1$. The cells analyzed fell into two groups: those that bound Fn with only low affinity (Kd>1 μM), e.g., K562, THP1, U937, and peripheral blood T cells, and those that bound with moderate affinity (Kd~100 nM), e.g., CHO, WI-38, and MG63 cells. The low affinity $\alpha_5\beta_1$ integrin was intrinsically functional since it bound Fn after "activation" with the 8A2 monoclonal antibody (Faull et al., J. Cell Biol. 121:155–162, 1993). Specificity of Fn binding to high affinity $\alpha_5\beta_1$ was verified by inhibition with an anti-$\alpha_5$ antibody (FIG. 1A; $^{125}$I-Fn (50 nM) was incubated at 22° C. with CHO or K562 cells. After 30 minutes, bound Fn was assessed by centrifugation through a sucrose cushion, as described below. $\alpha_5\beta_1$-specific binding was established by blocking Fn binding to the CHO cells with PB1, an anti-hamster $\alpha_5$ antibody. Binding to K562 cells was induced by addition of 20 nM "activating" antibody (8A2) and was inhibited by the anti-$\alpha_5$ antibody (BIIG2). The levels of surface expression of $\alpha_5\beta_1$ in the two cell types was also determined (FIG. 1B; CHO and K562 cells were stained with irrelevant mouse IgG (dotted line), an anti-$\beta_1$ antibody (K562:SA2, CHO:7E2) (solid line), or an anti-$\alpha_5$ antibody (K562:BIIG2, CHO:PB1) (dashed line) and then analyzed by flow cytometry as described below).

To determine whether spontaneous high affinity Fn binding to $\alpha_5\beta_1$ is an active process, we treated CHO cells with a combination of inhibitors of oxidative phosphorylation (NAN$_3$) and anaerobic glycolysis (2-deoxyglucose). This resulted in loss of specific high affinity Fn binding. This effect was partially reversible since washout of the metabolic inhibitors resulted in restoration of 75% of the high affinity binding (FIG. 1C; the binding of $^{125}$I-Fn to CHO cells (Resting), to cells incubated in medium containing 2 mM deoxyglucose and 0.1% sodium azide (DOG/Az), or to cells washed free of these inhibitors and returned to glucose-containing medium (Wash+Glc) was determined. Specificity of binding to $\alpha_5\beta_1$ was verified by inhibition with the PB1 antibody). Thus, high affinity Fn binding to integrin $\alpha_5\beta_1$ is cell type-specific and an active cellular process.

The cytoplasmic domains of $\alpha_5\beta_1$ confer an energy-dependent high affinity state on $\alpha_{IIb}\beta_3$ in some cells but not others.

To determine whether the cytoplasmic domains of $\alpha_5\beta_1$ are involved in cell type-specific affinity modulation, we generated chimeras in which the cytoplasmic domains of $\alpha_{IIb}$ and $\beta_3$ were replaced with the corresponding sequences from $\alpha_5$ and $\beta_1$ (FIG. 2; Amino acid sequences of wild type and variant integrin cytoplasmic domains. Single letter amino acid code is used. The arrows underneath the $\alpha_{IIb}$ (residue 990) and $\beta_3$ (residue 727) sequences denote the position at which chimeric cytoplasmic domains were joined to the extracellular and transmembrane domains of $\alpha_{IIb}$ and $\beta_3$. The position of stop codons producing cytoplasmic truncations are noted by triangles, while the $S^{752} \rightarrow P$ point mutation in $\beta_3$ is indicated. The residues deleted in the $\alpha_L \Delta$ cytoplasmic domain are overlain by the heavy line). The $\alpha$ and $\beta$ chimeras were co-transfected into CHO or K562 cells, and the affinity state of the extracellular $\alpha_{IIb}\beta_3$ reporter group was assayed by binding of PAC1, an antibody specific for the high affinity state of $\alpha_{IIb}\beta_3$ (Shattil et al., J. Biol. Chem. 260:11107–11114, 1985). The double chimera bound PAC1 when it was expressed in CHO cells. Since wild-type $\alpha_{IIb}\beta_3$ does not bind PAC1 when expressed in CHO cells (O'Toole et al., Cell Regulation 1:883–893, 1990), it is concluded that the $\alpha_5\beta_1$ cytoplasmic domains conferred the high affinity state on $\alpha_{IIb}\beta_3$. In sharp contrast, PAC1 did not bind to the double chimera in K562 cells. However, PAC1 bound after addition of an activating antibody, anti-LIBS6, confirming that the ligand binding site was intact (FIG. 3A; CHO or K562 cells were stably transfected with chimeras containing the cytoplasmic domains of $\alpha_5$ and $\beta_1$ and the affinity state of the $\alpha_{IIb}\beta_3$ extracellular domain was assayed by its ability to bind PAC1 in the absence (solid line) or presence (dotted line) of 1 mM GRGDSP (SEQ ID NO: 13). Depicted are flow cytometry histograms. The K562 transfectants specifically bound PAC1 only after incubation with 6 [M activating antibody, anti-LIBS 6). Thus, the capacity of cell type-specific elements to modulate affinity depends on the integrin cytoplasmic domains.

Since K562 cells express endogenous $\alpha_{IIb}$ under certain conditions (Burger et al., Exp. Cell Res. 202:28–35, 1992), it was necessary to verify that all of the $\alpha_{IIb}$ expressed in the $\alpha$ chimera transfectants contained the $\alpha_5$ cytoplasmic domain. Immunoprecipitation of surface iodinated $\alpha$ chimera transfectants with an anti-$\alpha_5$ cytoplasmic domain antibody isolated polypeptides corresponding to transfected $\alpha_{IIb}$ and $\beta_3$ chimeras and endogenous $\alpha_{IIb}\beta_1$. In contrast, an anti-$\alpha_{IIb}$ cytoplasmic domain antibody immunoprecipitated no labeled polypeptides. An anti-$\alpha_5$ cytoplasmic antibody precipitated only endogenous $\alpha_5\beta_1$ from wild-type $\alpha_{IIb}\beta_3$ transfectants (FIG. 3B; Immunoprecipitation analysis of K562 transfectants. Wild type K562 cells (None) or stable transfectants expressing the $\alpha$ subunit noted in the figure ($\alpha_{IIb}\beta_5=\alpha_5$ cytoplasmic domain chimera) were surface iodinated, lysed, and immunoprecipitated with polyclonal antibodies specific for the $\alpha_5$ and $\alpha_{IIb}$ cytoplasmic domains, or with a monoclonal antibody reactive with the extracellular domain of $\alpha_{IIb}\beta_3$ (2G12). Immunoprecipitates were resolved by SDS-PAGE and constituent polypeptides were visualized by autoradiography).

In addition, we confirmed fidelity of expression at the mRNA level. Reverse transcriptase-polymerase chain reaction was performed using a 5' primer specific for the extracellular domain of $\alpha_{IIb}$ and 3' primers specific for cytoplasmic domains of $\alpha_{IIb}$ or $\alpha_5$. A specific 393 base pair band was observed from $\alpha$ chimera transfectants when primed with the 3' $\alpha_{IIb}$ oligonucleotide. No bands were observed when inappropriate 3' primers were used (FIG. 3C; Reverse transcriptase-polymerase chain reaction (RT-PCR) analysis. RT-PCR was performed as described below with the 5' 2bsf primer and 3' primers specific for $\alpha_{IIb}$ or $\alpha_5$ 3' untranslated sequences, and the amplified products were analyzed by agarose gel electrophoresis).

As was shown in FIG. 1, high affinity Fn binding to $\alpha_5\beta_1$ depends on active cellular metabolism. We therefore analyzed the effects of $NaN_3$ and 2-deoxyglucose on the affinity state of the double chimera in CHO cells. These inhibitors blocked both PAC1 (FIG. 4A; Stable CHO transfectants expressing the $\alpha_5$ and $\beta_1$ cytoplasmic domain chimeras were assayed for PAC1 binding in the absence (solid line) and presence (dotted line) of 2 mM GRGDSP (SEQ ID NO: 13) by flow cytometry. Transfectants incubated with 2 mg/ml deoxyglucose and 0.1% $NaN_3$ (Inhibitors), as described below, manifested loss of specific binding. Addition of 6 μM anti-LIBS 2 (Inhibitors+Anti-LIBS2) or washout of these inhibitors (Inhibitors+washout) and return to glucose-containing medium reconstituted specific PAC1 binding) and Fg (FIG. 4B; Stable CHO transfectants expressing the cytoplasmic domains noted below the graph were analyzed for Fg binding as described below. Constitutive binding to transfectants expressing the $\alpha_5$ and $\beta_1$ chimeras was inhibited by 2 mg/ml deoxyglucose plus 0.1% $NAN_3$; binding to transfectants expressing the $\alpha_{IIb}\Delta991$ or $\alpha_L\Delta$ variant was not inhibited (see below)) binding. Anti-LIBS2, an activating antibody (Frelinger et al., J. Biol. Chem. 266:17106–17111, 1991), restored high affinity binding. Furthermore, the metabolic blockade was reversible since high affinity ligand binding reappeared after the inhibitors were washed out (FIG. 4A). These results show that $\alpha_5\beta_1$ cytoplasmic sequences confer a cell type-specific, energy-dependent, high affinity state on the extracellular domain of $\alpha_{IIb}$ $\beta_3$.

Both $\alpha$ and $\beta$ cytoplasmic domains are involved in affinity modulation.

To determine which cytoplasmic domain specified the high affinity state in CHO cells, we transfected each subunit chimera with a complementary wild-type subunit. Transfectants expressing both $\alpha$ and $\beta$ chimeras or expressing the chimeric $\alpha$ but wild-type $\beta_3$ subunits bound PAC1. In contrast, cells expressing the $\beta$ chimera with wild-type $\alpha_{IIb}$ were in a low affinity state and bound PAC1 only after addition of anti-LIBS2 (FIG. 5A; CHO cells were transiently transfected with subunits comprised of the extracellular and transmembrane domains of $\alpha_{IIb}$ and $\beta_3$ joined to the indicated cytoplasmic domains. The affinity state of the extracellular portion of $\alpha_{IIb}$ $\beta_3$ was assessed by PAC1 binding. Binding was analyzed in the absence (solid line) or presence (dotted line) of GRGDSP (SEQ ID NO: 13) peptide. Graphs of cells incubated in the presence of 6 μM anti-LIBS2 are depicted in the lower panels. Specific PAC1 binding is present in both transfectants containing the $\beta_5$ cytoplasmic domain irrespective of the presence of either the $\beta_3$ or $\beta_1$ cytoplasmic domain on the $\beta_3$ subunit. In contrast, PAC1 specifically bound to those transfectants containing the $\alpha_{IIb}$ cytoplasmic domain only in the presence of the activating antibody, anti-LIBS2). These results show that $\alpha$ cytoplasmic sequences are involved in specifying affinity state.

To find out if the $\beta$ subunit was also involved in specifying the high affinity state in CHO cells, we constructed two $\beta_3$ cytoplasmic variants, $\beta_3\Delta724$ and $\beta_3$ ($S^{752}\rightarrow P$). The former is a truncation mutant that ends at $D^{723}$, while the latter contains a single nucleotide alteration resulting in a $Ser^{752}\rightarrow Pro$ substitution (FIG. 2). These $\beta_3$ cytoplasmic domain mutants were co-transfected with the $\alpha$ chimera. In contrast to wild-type $\beta_3$, coexpression of either $\beta_3$ variant with chimeric $\alpha$ resulted in a receptor that failed to bind PAC1 constitutively (FIG. 5B; Stable CHO cell lines expressing recombinant $\alpha_{IIb}\beta_3$ chimeras containing the noted cytoplasmic domains were reacted with PAC1 and bound antibody was detected by flow cytometry as described below. Binding was analyzed in the absence (solid line) or presence (dotted line) of GRGDSP (SEQ ID NO: 13) peptide. The intrinsic functionality of each construct was assessed by PAC1 binding in the presence of 6 μM anti-LIBS2 (lower panels). A $\beta_3$ cytoplasmic truncation ($\Delta724$) and single amino acid substitution($S^{752}\rightarrow P$) both abolished the constitutive high affinity state conferred by the cytoplasmic domain of $\alpha_5$). Thus, the cytoplasmic domain of the $\beta$ subunit as well as the $\alpha$ subunit is involved in affinity modulation.

Regulation of integrin affinity by the $\alpha$ subunit cytoplasmic domain is $\alpha$ subunit-specific These data established that the cytoplasmic domains of $\alpha_{IIb}$ and $\alpha_5$ specify different affinity states in CHO cells; $\alpha_{IIb}$ the low and $\alpha_5$ the high affinity state. To determine whether there are consensus "activation" sequences, we constructed chimeras with the cytoplasmic domains of six additional $\alpha$ subunits and analyzed their affinity state after co-transfection with $\beta_3$ into CHO cells. The $\alpha$ cytoplasmic domains of three other $\beta_1$ family members ($\alpha_2$, $\alpha_6 A$, $\alpha_6 B$) conferred PAC1 binding (FIG. 6A), while those chimeras containing $\alpha$ subunit cytoplasmic domains from $\beta_2$ ($\alpha_M$, $\alpha_L$) or $\beta_3$ ($\alpha_v$) families did not (FIG. 6A; Chimeric $\alpha$ subunits consisting of extracellular and transmembrane $\alpha_{IIb}$ with the indicated cytoplasmic domain were transiently co-transfected with $\beta_3$ into CHO cells. PAC1 binding was quantified by flow cytometry and the activation index was calculated as:

$$100*(F_O - F_R)/F_R$$

where:

$F_O$= Mean Fluorescence Intensity in the absence of inhibitor $F_R$= Mean Fluorescence Intensity in the presence of GRGDSP (SEQ ID NO: 13). Depicted are the Mean±S.D. of at least 3 independent experiments for each $\alpha$ chimera). The same result was obtained with the $\beta$ chimeras containing cytoplasmic domains of the relevant $\beta$ subunit partner ($\beta_1$ for $\alpha_2$, $\alpha_v$, $\alpha_6 A$, and $\alpha_6 B$ or $\beta_2$ for $\alpha_L$ and $\alpha_M$). Similar to the $\alpha_5$ chimera, constitutive PAC1 binding was also dependent upon the $\beta$ cytoplasmic domain. It was lost when the $\beta_2$, $\alpha_6 A$, or $\alpha_6 B$ chimeras were co-transfected with $\beta_3 \Delta 724$ or $\beta S752P$ (FIG. 6B; $\alpha$ subunit chimeras containing the indicated cytoplasmic sequences were co-transfected with a $\beta_3$ subunit in which the cytoplasmic domain was truncated ($\beta_3 \Delta 724$), contained the $S^{752} \rightarrow P$ mutation (S752P), or had been exchanged for the homologous region of $\beta_1$. PAC1 binding was analyzed as described for FIG. 6A. Mean±S.D. of at least 3 independent experiments for each $\alpha$ $\beta$ pair are depicted). Thus, the $\alpha$ subunit cytoplasmic domain designates integrinspecific affinity differences. The $\beta$ subunit cytoplasmic domain may be permissive for the high affinity state.

Deletion of conserved $\alpha$ cytoplasmic sequences results in high affinity ligand binding that is independent of metabolic energy and the $\beta$ subunit cytoplasmic domain We previously reported that constitutive ligand binding to $\alpha_{IIb}\beta_3$ results from a truncation of the cytoplasmic domain of $\alpha_{IIb}$ (O'Toole et al., Science 254:845–847, 1991). To identify the important deleted $\alpha_{IIb}$ cytoplasmic residues, we generated additional variants. Integrin $\alpha$ subunit cytoplasmic domains contain a highly conserved GFFKR (SEQ ID NO: 14) sequence at their $NH_2$-termini (FIG. 2). As previously reported (O'Toole et al., Science 254:845–847, 1991; Ylanne et al., J. Cell Biol. 122:223–233, 1993), the $\alpha_{IIb}\Delta 911$ truncation eliminates this motif and results in constitutive PAC1 binding whereas a truncation after the GFFKR (SEQ ID NO: 14) ($\alpha_{IIb}\Delta 996$) does not (FIG. 7A). This pinpoints the conserved motif as a regulator of integrin affinity. To test this idea, we removed the LGFFK (SEQ ID NO: 15) residues from the cytoplasmic domain of an $\alpha_L$ cytoplasmic domain chimera (FIG. 2). This chimera was selected because it possesses the longest $\alpha$ cytoplasmic domain. Coexpression of this chimeric internal deletion mutant ($\alpha_L\Delta$) in CHO cells with $\beta_3$ resulted in high affinity PAC1 binding (FIG. 7B). Finally, to further exclude contributions from downstream $\alpha$ sequences, we generated a variant that contains a 24-residue random cytoplasmic sequence (FIG. 2). This construct ($\alpha_{Ra}$) also conferred high affinity binding when expressed in CHO cells with wild-type $\beta_3$ (FIG. 7A; Stable CHO cell lines were established by co-transfection of $\alpha_{IIb}$ containing the $\alpha$ cytoplasmic domain indicated in the figure with wild type $\beta_3$. PAC1 binding in the absence (solid line) and presence (dotted line) of GRGDSP (SEQ ID NO: 13) was assessed by flow cytometry. The $\alpha_{IIb}\Delta 991$ transfectant, which lacks GFFKR (SEQ ID NO: 14), specifically binds PAC1. In contrast the $\alpha_{IIb}\Delta 996$ transfectant, which retains GFFKR (SEQ ID NO: 14), binds only after "activation" with anti-LIBS2. Replacement of the $\alpha_{IIb}$ cytoplasmic domain with random sequence also induces PAC1 binding ($\alpha_{Ra}$)).

To gain insight into the mechanisms of high affinity binding conferred by the GFFKR (SEQ ID NO: 14) deletion mutants, we examined the requirements for cellular metabolism and $\beta$ cytoplasmic sequences. In contrast to the constitutively active chimeras, high affinity PAC1 binding in the GFFKR (SEQ ID NO: 14) deletion variants was maintained when they were coexpressed with the truncated $\beta_3$ subunit (FIG. 7B). In addition, in contrast to transfectants expressing constitutively active $\alpha$ chimeras, transfectants expressing the GFFKR (SEQ ID NO: 14) deletion retained high affinity for Fg and PAC1 (FIG. 7B) when treated with the metabolic inhibitors $NaN_3$ and 2-deoxyglucose. Finally, the $\alpha_L\Delta$ mutant conferred cell-type independent activation, since it was active in K562 (FIG. 7B; CHO cells were transiently transfected with chimeras of the extracellular and transmembrane domains of $\alpha_{IIb}\beta_3$ joined to the cytoplasmic domains indicated in the figure. Specific PAC1 binding to the population of cells expressing $\alpha_{IIb}\beta_3$ was detected as in FIG. 7A. A GFFKR (SEQ ID NO: 14) "loop out" mutant manifested PAC1 binding ($\alpha_{LA}\beta_3$) that was maintained in the presence of 0.1% $NaN_3$ and 2 mM 2-deoxyglucose (inhibitors). This treatment abolished ligand binding to an $\alpha_{IIb}\beta_3$ chimera bearing the cytoplasmic domain of $\alpha_5\beta_1$. High affinity state was also maintained despite an extensive deletion of the $\beta_3$ cytoplasmic domain ($\alpha_{LA}\beta\Delta 724$) that disrupted PAC1 binding to the $\alpha_5\beta_1$ chimera. Similar results were obtained with $\alpha_{IIb}\Delta 991$ and $\alpha_{Ra}$ transfectants. A stable K562 cell line bearing the a GFFKR (SEQ ID NO: 14) deletion mutant specifically bound PAC1 ($\alpha_{LA}\beta_3$), but the $\alpha_5\beta_1$ chimera was not active in these cells) and COS, as well as in CHO cells. Thus, deletions in the highly conserved GFFKR (SEQ ID NO: 14) motif resulted in a cell type-independent high affinity state that was resistant to metabolic inhibitors and truncation of the $\beta$ subunit.

Experimental Procedures:

Antibodies and reagents.

The anti-$\alpha_{IIb}\beta_3$ antibody D57 was produced using previously described methods (Frelinger et al., J. Biol. Chem. 265:6346–6352, 1990). It binds to Chinese hamster ovary (CHO) cells transfected with $\alpha_{IIb}\beta_3$, but not $\alpha_v\beta_3$, and does not block Fg binding to $\alpha_{IIb}\beta_3$. This antibody was biotinylated with biotin-N-hydroxy-succinimide (Sigma Chemical, St. Louis, Mo.) according to manufacturer's directions. The $\alpha_{IIb}\beta_3$ complex specific antibody, 2G12 (Plow et al., Blood 66:724–727, 1985), was used as dilutions of ascites fluid. The anti-hamster $\alpha_5$ (PB1) and anti-$\beta_1$ (7E2) antibodies, the $\beta_1$ activating antibody, 8A2 (Kovach et al., J. Cell Biol. 116:499–509, 1992); a human anti-$\alpha$ antibody, BIIG2 (Werb et al., J. Cell Biol. 109:877–889, 1989); a polyclonal antipeptide antibody against the cytoplasmic domain of human $\alpha_5$ (Hynes et al., J. Cell Biol. 109:409–420, 1989); anti-LIBS6, anti-LIBS2, and anti-$\alpha_{IIb}$ cytoplasmic domain antibodies (Frelinger et al., J. Biol. Chem. 265:6346–6352, 1990; O'Toole et al., Science 254:845–847, 1991); and PAC1 (Shattil et al., J. Biol. Chem. 260:11107–11114, 1985) have been described previously. Glucose and 2-deoxyglucose were purchased from Sigma and sodium azide was purchased from Fisher Scientific Co. (Pittsburgh, Pa.). The peptide GRGDSP (SEQ ID NO: 13) was obtained from Peninsula Laboratories (Belmont, Calif.). Its purity and composition were verified by high performance liquid chromatography and fast atom bombardment mass spectroscopy.

Cell culture and transfection.

The human cell lines K562, U937, W1-38, and MG63 were obtained from the American Type Culture Collection (ATCC; Rockville, Md.) and maintained in RPMI 1640 media (Biowhittaker, Walkersville, Md.) containing 10% fetal bovine serum (Biowhittaker, Walkersville, Md.) 1% glutamine (Sigma) and 1% penicillin and streptomycin (Sigma). THP-1 cells (ATCC; Rockville, Md.) were maintained in the same medium with the addition of 10 mM Hepes and 20 mM 2-mercaptoethanol. Chinese hamster ovary (CHO) cells (ATCC; Rockville, Md.) were maintained in DMEM media (Biowhittaker; Walkersville, MD) with 10% fetal calf serum, the above noted antibiotics, and 1% non-essential amino acids (Sigma). Human T lymphocytes were purified from peripheral blood of normal donors by centrifugation on a Ficoll-Paque gradient (Pharmacia Fine Chemicals, Piscataway, N.J.), panning for monocytes on serum-coated dishes, and passage over a nylon wool column.

CHO cells were transiently transfected by electroporation. Cells in log phase growth were harvested with trypsin (Irvine Scientific), washed with PBS, and combined with appropriate cDNAs (10 µg of each subunit). $3 \times 10^7$ cells in 0.5 ml of growth media were electroporated at 350 volts, 960 µF, in a BTX (BTX, San Diego, Calif.) electroporator. Media were changed after 24 hours and cells analyzed for surface expression, or PAC1 binding after 48 hours. Stable CHO transfectants were established as above with co-transfection of 0.6 µg of CDNeo. After 48 hours, these cells were selected for 2 weeks in 700 µ G418 (Gibco) and clonal lines were established by single cell sorting in a FACStar (Becton Dickinson). Stable K562 transfectants were established by electroporation of $1 \times 10^7$ cells in 0.8 ml of PBS at 300 volts and 500 µF. After 48 hours the cells were maintained in media containing 1 mg/ml G418, and clonal lines established by limiting dilution cloning.

Flow Cytometry

Surface expression of integrins was analyzed by flow cytometry with specific antibodies as described (Loftus et al., Science 249:915–918, 1990; O'Toole et al., Blood 74:14–18, 1989). Briefly, $5 \times 10^5$ cells were incubated on ice for 30 minutes with primary antibody, washed, and incubated on ice for 30 minutes with an FITC-conjugated goat anti-mouse (Tago, Burlingame, Calif.) secondary antibody. Cells were pelleted, resuspended, and analyzed on a FACScan (Becton Dickinson). PAC1 binding was analyzed by two color flow cytometry. Cell staining was carried out in Tyrode's buffer (Ginsberg et al., Blood 55:661–668, 1980) containing 2 mM $MgCl_2$ and $CaCl_2$ and 1 mg/ml BSA (Sigma) and dextrose. Single cell suspensions were obtained by harvesting with 3.5 mM EDTA, incubating for 5 minutes in 1 mg/ml TPCK trypsin (Worthington), and diluting with an equal volume of Tyrode's buffer containing 10% fetal calf serum and 0.1% soybean trypsin inhibitor (Sigma). After washing, $5 \times 10^5$ cells were incubated in a final volume of 50 µl containing 0.1% PAC1 ascites fluid in the presence or absence of 1 mM GRGDSP (SEQ ID NO: 13) peptide. After a 30 minute incubation at room temperature, cells were washed with cold Tyrode's buffer and then incubated on ice with biotinylated antibody D57. After 30 minutes cells were washed and then incubated on ice with Tyrode's buffer containing 10% FITC-conjugated goat anti-mouse IgM (Tago) and 4% phycoerythrin-streptavidin (Molecular Probes Inc., Junction City, Oreg.). Thirty minutes later, cells were diluted to 0.5 ml with Tyrode's buffer and analyzed on a FACScan (Becton Dickinson) flow cytometer as described (O'Toole et al., Cell Regulation 1:883–893, 1990). PAC1 binding (FITC staining) was analyzed only on a gated subset of cells positive for $\alpha_{IIb}\beta_3$ expression (phycoerythrin staining). To define affinity state, histograms depicting PAC1 staining in the absence or presence of 1 mM GRGDSP (SEQ ID NO: 13) were superimposed. Since RGD peptides are inhibitors of PAC1 binding to $\alpha_{IIb}\beta_3$ (Bennett et al., J. Biol. Chem. 263:12948–12953, 1988), a rightward shift in the histogram in the absence of RGD peptide is indicative of the presence of high affinity $\alpha_{IIb}\beta_3$ integrin. To compare the effects of multiple α subunits, pooling of data involving experiments from different days was required. To do this, a numerical activation index was defined as:

$$100*(F_O-F_R)/F_R$$

where:

$F_O$=Mean Fluorescence Intensity in the absence of inhibitor, and $F_R$=Mean Fluorescence Intensity in the presence of GRGDSP (SEQ ID NO: 13).

DNA Constructs

The generation of CDM8 constructs encoding $\alpha_{IIb}$, $\alpha_{IIb}\Delta991$, $\alpha_{IIb}\Delta996$, $\beta_3$, and $\beta_3\Delta728$ has been previously described (O'Toole et al., Blood 74:14–18, 1989; O'Toole et al., Science 254:845–847, 1991; Ylanne et al., J. Cell Biol. 22:223–233, 1993). The $\beta_3$ truncation, $\Delta724$, and amino acid substitution, $S^{752} \rightarrow p$, were first generated in BS3a (O'Toole et al., Blood 74:14–18, 1989) by oligonucleotide-directed mutagenesis (Kunkel, Proc. Natl. Acad. Sci. USA 82:488–492, 1985), digested with HincII to isolate coding sequences, ligated to BstXI linkers (InVitrogen) and subcloned into the BstXI sites of CDM8. The $\beta_3$ chimera, containing the $\beta_1$ cytoplasmic domain, was constructed by first generating an EcoRI site at bases 2387–2392 of $\beta_1$ cDNA sequence. After HindIII digestion, a 400 bp fragment containing the complete $\beta_1$ cytoplasmic domain and partial 3' non-coding sequences was isolated and subcloned into the HindIII site of CDM8. This construct was then digested with EcoRI and ligated with a 2.2 kb EcoRI fragment from CD3a (O'Toole et al., Blood 74:14–18, 1989) containing its transmembrane and extracellular domains. $\beta_2$ cytoplasmic sequences were first isolated by the polymerase chain reaction (PCR) from a $\beta_2$ cDNA and then subcloned into the MluI and XhoI sites of CDM8. The $\beta_2$ cytoplasmic domain chimera was then generated by digestion with MluI and HindIII and ligation with a corresponding MluI-HindIII fragment from CD3a containing its extracellular and transmembrane sequences. Chimeric α subunits were generated following a previously described strategy (O'Toole et al., Science 254:845–847, 1991). Cytoplasmic sequences from $\alpha_v$, $\alpha_M$, $\alpha_2$, $\alpha_6A$, and $\alpha_6B$ were isolated from the appropriate cDNA clones by PCR (Loftus et al., Science 249:915–918, 1990). Amplified products were digested with HindIII and XbaI and subcloned into HindIII and XbaI cut CDM8. After digesting with HindIII, these constructs were ligated with a HindIII fragment from CD2b (O'Toole et al., Blood 74:14–18, 1989) containing its extracellular and transmembrane domains. PCR oligonucleotides for $\alpha_L\Delta$ were designed to omit the VGFFK (SEQ ID NO: 16) sequence. Its construction followed the procedure for other α chimeras. The $α_{Ra}$ variant was made by first generating a SalI site in CD2b coding sequences corresponding to bases 3061–3066. This vector was then digested with SalI and XbaI and ligated to a SalI-XbaI Bluescript vector sequence (bases 674–731). All constructs were verified by DNA sequencing and purified by CsCl centrifugation before transfection. Oligonucleotides were synthesized on a Model 391 DNA Synthesizer (Applied Biosystems).

Ligand Binding

The binding of $^{125}$I-Fg or $^{125}$I-Fn to cultured cells was carried out as described (O'Toole et al., Cell Regulation 1:883–893, 1990; Faull et al., J. Cell Biol. 121:155–162, 1993). Cells were harvested with EDTA and trypsin as described above for flow cytometry analysis, and resuspended in a modified Tyrode's buffer (150 mM NaCl, 2.5 mM KCl, 2 mM NaHCO$_3$, 2 mM MgCl$_2$, 2 mM CaCl$_2$, 1 mg/ml BSA, and 1 mg/ml dextrose). A typical assay included 120 μl of cells (2×10$^6$ cells per tube), 40 μl of radiolabelled protein, and 40 μl of inhibitor (GRGDSP (SEQ ID NO: 13) peptide, blocking antibodies) or agonist (activating antibody). After 30 minutes at room temperature 50 μl aliquots were layered in triplicate on 0.3 ml of 20% sucrose and centrifuged for 3 minutes at 12,000 rpm. $^{125}$I-labelled protein associated with the cell pellet was determined by scintillation spectrometry. Non-saturable binding was determined in the presence of 2 mM GRGDSP (SEQ ID NO: 13) peptide. Data were fit to equilibrium binding models by the nonlinear least squares curve-fitting LIGAND program (Munson and Rodbard, Anal. Biochem. 107:220–239, 1980). In binding experiments utilizing metabolic inhibitors, the cells were first incubated with 2 mg/ml 2-deoxyglucose and 0.1% sodium azide for 30 minutes at room temperature before addition of radiolabelled ligand. In washout experiments, cells treated in this way were washed, incubated with Tyrode's buffer containing 1 mg/ml dextrose for 30 minutes at room temperature, and then analyzed for ligand binding.

Immunoprecipitation

Transfectants were surface labelled by the Iodogen method according to the manufacturer's instructions (Pierce Chemical) and solubilized in lysis buffer (10 mM Hepes (pH 7.5), 0.15M NaCl, 50 mM octylglucoside, 1 mM CaCl$_2$, 1 mM MgCl$_2$, 1 mM phenylmethylsulfonyl fluoride, 0.1 mM leupeptin, and 10 mM N-ethylmaleimide). Cell extracts were immunoprecipitated with polyclonal antiserum directed against the $α_{IIb}$ or $α_5$ cytoplasmic domains, and a monoclonal antibody against the $α_{IIb}β_3$ complex (2G12). The antibodies were attached to preswollen protein A-Sepharose beads (Pharmacia LKB Biotechnology Inc.) by incubation at 4° C. overnight. The antibody-conjugated Sepharose beads were washed, pelleted by centrifugation, and then incubated with the detergent lysates from the surface labelled cells overnight with shaking. The Sepharose beads were washed extensively in lysis buffer, resuspended in sample buffer (Laemmli, Nature 227:680–685, 1970), and boiled for 5 minutes. After centrifugation, the precipitated proteins were resolved by SDS-PAGE (non-reducing, 7.5% acrylamide gels). Gels were dried and radiolabelled polypeptides were visualized by autoradiography.

Polymerase Chain Reaction

Total RNA was isolated from 10$^6$ transfected cells using the RNAzol reagent (Cinna Biotecx). First strand cDNA synthesis from 5 μg of RNA was performed with the cDNA cycle kit (Invitrogen, San Diego, Calif.) using oligo dT as a primer. Coding sequences downstream of the $α_{IIb}$ transmembrane region were specifically amplified with a 5' primer specific for transmembrane $α_{IIb}$ (2bsf: CGGGCCT-TGGAGGAGAGGGCCATTC (SEQ ID NO: 17)) and 3' primers specific for the cytoplasmic sequences of $α_{IIb}$ ($α_{IIb}$ cYt: CTCTGTTGGGAGGGAAACGA (SEQ ID NO: 18); and $α_5$ $α_5$scYt: TGTAAACAAGGGTCCTTCAC (SEQ ID NO: 19)). Amplified products were analyzed by agarose gel electrophoresis.

Use of Inhibitors

The invention provides methods for identifying compounds which inhibit integrin activation. Integrins are surface adhesive molecules which play roles in a number of physiological processes, including activation of the immune response, inflammation, and thrombosis. Thus, the inhibitors of the invention can be used in methods to modulate the above-listed physiological processes. In addition to playing a role in the migration of normal cells, integrins are also involved in the migration and metastasis of tumor cells. Thus, the inhibitors of the invention may be useful in treating patients with tumors or cancer.

The inhibitors can be administered to the patient by any appropriate method suitable for the particular inhibitor, e.g., orally, intravenously, parenterally, transdermally, or transmucosally. Therapeutic doses are determined specifically for each inhibitor, most administered within the range of 0.001–100.0 mg/kg body weight, or within a range that is clinically determined as appropriate by those skilled in the art.

Other Embodiments

From the above description, one skilled in the art can easily ascertain the essential characteristics of the present invention, and without departing from the spirit and scope thereof, can make various changes and modifications of the invention to adapt it to various usages and conditions. Other embodiments are in the claims set forth below.

What is claimed is:

1. A method of measuring the ability of a candidate compound to inhibit activation of a target integrin mediated by the cytoplasmic domain of said target integrin, said method comprising the steps of:
   (a) providing a cell expressing a chimeric integrin comprising the extracellular and transmembrane domains of a reporter integrin fused to the cytoplasmic domain of said target integrin;
   (b) culturing said cell in the presence of said candidate compound and under conditions in which said chimeric integrin would be activated in the absence of an inhibitor of integrin activation;
   (c) contacting said cell with a ligand that binds to said reporter integrin, only when said reporter integrin is activated; and
   (d) determining the level of said ligand bound to said reporter integrin, wherein a decrease in ligand binding indicates that the compound is an inhibitor of activation of said target integrin; and (e) determining the level of said ligand bound to said reporter integrin in the presence of an activating antibody, wherein an increase in ligand binding in the presence of the activating antibody compared to the ligand binding in the absence of the activating antibody indicates that the canditate compound is an inhibitor of activation of said target integrin.

2. The method of claim 1, wherein said reporter integrin is $\alpha_{IIb}\beta_3$.

3. The method of claim 2, wherein the subunit of said target integrin is $\alpha_5$, $\alpha_2$, $\alpha_{6a}$, or $\alpha_{6b}$.

4. The method of claim 3, wherein the $\beta$ subunit of said target integrin is $\beta_3$.

5. The method of claim 2, wherein said target integrin is $\alpha_5\beta_1$.

6. The method of claim 1, wherein said target integrin is selected from the group consisting of $\alpha_v\beta_3$, $\alpha_M\beta_2$, $\alpha_L 2$, $\alpha_2\beta_1$, $\alpha_5\beta_1$, $\alpha_{6A}\beta_1$, $\alpha_{6B}\beta_1$, $\alpha_{IIb}\beta_3$, and $\alpha_4\beta_1$.

7. The method of claim 1, wherein said ligand is an antibody.

8. The method of claim 7, wherein said antibody is PAC1.

9. The method of claim 1, wherein said ligand is fibrinogen.

* * * * *

UNITED STATES PATENT AND TRADEMARK OFFICE
CERTIFICATE OF CORRECTION

PATENT NO. : 5,523,209

DATED : June 4, 1996

INVENTOR(S) : Mark H. Ginsberg and Timothy E. O'Toole

It is certified that error appears in the above-identified patent and that said Letters Patent is hereby corrected as shown below:

On the title page, under "OTHER PUBLICATIONS", col. 2, line 11, "Frelinger et al.", replace "Comformers of Integrin" with --Conformers of Integrin--;

Under "OTHER PUBLICATIONS", page 2, line 21, "O'Toole et al.", replace "1:883t14 893 (1990)" with --1:883-893 (1990)--;

Col. 1, line 26, replace "J. Biolo Chem." with --J. Biol. Chem.--;

Col. 1, line 58, replace "Duet al." with --Du et al.--;

Col. 1, line 64, replace "Biolo" with --Biol.--;

Col. 2, line 35, replace "$\alpha_v \equiv_3$," with --$\alpha_v \beta_3$--;

Col. 4, line 18, replace "$\alpha_1$" with --$\beta_1$--;

Col. 6, line 25, replace "(K562:SA2," with --(K562:8A2,--;

Col. 7, line 13, replace "6[M activating antibody," with --6$\mu$M activating antibody,--;

Col. 8, line 29, replace "$\beta_5$" with --$\alpha_5$--;

UNITED STATES PATENT AND TRADEMARK OFFICE
CERTIFICATE OF CORRECTION

PATENT NO. : 5,523,209

DATED : June 4, 1996

INVENTOR(S) : Mark H. Ginsberg and Timothy E. O'Toole

It is certified that error appears in the above-identified patent and that said Letters Patent is hereby corrected as shown below:

Col. 9, line 24, replace "$\beta_2$" with --$\alpha_2$--;

Col. 9, line 34, replace "integrinspecific" with --integrin-specific--;

Col. 11, line 35, replace "700 $\mu$ G418 (Gibco)" with --700 $\mu$g/ml G418 (Gibco)--;

Col. 14, line 21, replace "cYt" with --cyt--;

Col. 14, line 22, replace "$\alpha_5$scYt" with --$\alpha_5$cyt--;

Col. 24, claim 1, line 3, correct the spelling of "candidate";

Col. 24, claim 3, line 8, replace "wherein the subunit of said target integrin" with --wherein the $\alpha$ subunit of said target integrin--;

Col. 24, claim 6, line 15, replace "$\alpha_L 2$," with --$\alpha_L \beta_2$,--.

Signed and Sealed this

Twenty-fourth Day of December, 1996

Attest:

BRUCE LEHMAN

*Attesting Officer*    *Commissioner of Patents and Trademarks*